United States Patent [19]
Tomita et al.

[11] Patent Number: 5,532,339
[45] Date of Patent: Jul. 2, 1996

[54] FUSION PROTEIN BETWEEN HUMAN MACIF AND A HETEROLOGOUS PI ANCHOR DOMAIN

[75] Inventors: Motowo Tomita, Kanagawa; Yuji Sugita, Saitama; Toshiyuki Takemoto, Saitama; Kiyoshi Furuichi, Saitama; Makoto Takayama; Ko Yasukawa, both of Tokyo; Katsuhisa Ito, Saitama; Noboru Yamaji; Shinya Yano, both of Tokyo, all of Japan

[73] Assignee: Yamanouchi Pharmaceutical Co., Ltd., Tokyo, Japan

[21] Appl. No.: 291,339

[22] Filed: Aug. 17, 1994

Related U.S. Application Data

[63] Continuation of Ser. No. 21,724, Feb. 22, 1993, abandoned, which is a continuation of Ser. No. 510,610, Apr. 18, 1990, abandoned.

[30] Foreign Application Priority Data

| Apr. 21, 1989 | [JP] | Japan | 1-103088 |
| Jul. 12, 1989 | [JP] | Japan | 1-179933 |
| Sep. 6, 1989 | [JP] | Japan | 1-230983 |
| Sep. 13, 1989 | [JP] | Japan | 1-238246 |
| Sep. 21, 1989 | [JP] | Japan | 1-247818 |
| Oct. 27, 1989 | [JP] | Japan | 1-281197 |

[51] Int. Cl.$^6$ .......................... C07K 14/47; C07K 19/00
[52] U.S. Cl. .......................... 530/350; 530/324; 530/380; 435/69.7
[58] Field of Search .......................... 530/350, 324, 530/380, 395; 435/69.1, 69.6, 69.7

[56] References Cited

U.S. PATENT DOCUMENTS

| 4,935,494 | 6/1990 | Miller | 530/345 |
| 5,109,113 | 4/1992 | Caras et al. | 530/350 |

OTHER PUBLICATIONS

Kieffer, B., et al., *Biochem.* 33:4471–4482, 1994.
Ferguson, M. A. J., et al. *Ann. Rev. Biochem.* 57:285–320, 1988.
Journal of Biochemistry, vol. 104, No. 4, Oct. 1988 pp. 633–637, Y. Sugita et al.
Okada et al. "20 kDa Homologous Restriction Factor . . . " BBRC v. 162(3) pp. 1553–1559 Aug. 15, 1989.
Davies et al. "CD59, An LY-6-Like Protein . . . " J. Exp. Med. vol. 170, pp. 637–654. Sep. 1, 1989.
Stefanova et al "Characterization of a Broadly Expressed Human Leukocyte Surface Antigen . . . " Mol. Imm. v. 26(2) pp. 153–161 Feb. 1989.
Seed et al. "Molecular Cloning of the CD2 Antigen . . . " Proc. Natl. Acad. Sci. USA vol. 84 pp. 3365–3369 (May 1987).

*Primary Examiner*—Garnette D. Draper
*Assistant Examiner*—David L. Fitzgerald
*Attorney, Agent, or Firm*—Burgess, Ryan and Wayne

[57] ABSTRACT

Fusion proteins comprising the extracellular domain of the human MACIF (Membrane Attack Complex Inhibition Factor) gene product and a heterologous phosphatidylinositol (PI) anchor domain are provided.

1 Claim, 17 Drawing Sheets

5⋯TTCTGTGGACAATCACA

| -25 | -24 | -23 | -22 | -21 |
|---|---|---|---|---|
| ATG | GGA | ATC | CAA | GGA |

| -20 | -19 | -18 | -17 | -16 | -15 | -14 | -13 | -12 | -11 |
|---|---|---|---|---|---|---|---|---|---|
| GGG | TCT | GTC | CTG | TTC | GGG | GTA | CTC | CTC | GTC |

| -10 | -9 | -8 | -7 | -6 | -5 | -4 | -3 | -2 | -1 |
|---|---|---|---|---|---|---|---|---|---|
| CTG | GCT | GTC | TTC | TGC | CAT | TCA | GGT | CAT | AGC |

| 1 | 2 | 3 | 4 | 5 | 6 | 7 | 8 | 9 | 10 |
|---|---|---|---|---|---|---|---|---|---|
| CTG | CAG | TGC | TAC | AAC | TGT | CCT | AAC | CCA | ACT |

| 11 | 12 | 13 | 14 | 15 | 16 | 17 | 18 | 19 | 20 |
|---|---|---|---|---|---|---|---|---|---|
| GCT | GAC | TGC | AAA | ACA | GCC | GTC | AAT | TGT | TCA |

| 21 | 22 | 23 | 24 | 25 | 26 | 27 | 28 | 29 | 30 |
|---|---|---|---|---|---|---|---|---|---|
| TCT | GAT | TTT | GAT | GCG | TGT | CTC | ATT | ACC | AAA |

| 31 | 32 | 33 | 34 | 35 | 36 | 37 | 38 | 39 | 40 |
|---|---|---|---|---|---|---|---|---|---|
| GCT | GGG | TTA | CAA | GTG | TAT | AAC | AAG | TGT | TGG |

| 41 | 42 | 43 | 44 | 45 | 46 | 47 | 48 | 49 | 50 |
|---|---|---|---|---|---|---|---|---|---|
| AAG | TTT | GAG | CAT | TGC | AAT | TTC | AAC | GAC | GTC |

| 51 | 52 | 53 | 54 | 55 | 56 | 57 | 58 | 59 | 60 |
|---|---|---|---|---|---|---|---|---|---|
| ACA | ACC | CGC | TTG | AGG | GAA | AAT | GAG | CTA | ACG |

| 61 | 62 | 63 | 64 | 65 | 66 | 67 | 68 | 69 | 70 |
|---|---|---|---|---|---|---|---|---|---|
| TAC | TAC | TGC | TGC | AAG | AAG | GAC | CTG | TGT | AAC |

| 71 | 72 | 73 | 74 | 75 | 76 | 77 | 78 | 79 | 80 |
|---|---|---|---|---|---|---|---|---|---|
| TTT | AAC | GAA | CAG | CTT | GAA | AAT | GGT | GGG | ACA |

| 81 | 82 | 83 | 84 | 85 | 86 | 87 | 88 | 89 | 90 |
|---|---|---|---|---|---|---|---|---|---|
| TCC | TTA | TCA | GAG | AAA | ACA | GTT | CTT | CTG | CTG |

| 91 | 92 | 93 | 94 | 95 | 96 | 97 | 98 | 99 | 100 |
|---|---|---|---|---|---|---|---|---|---|
| GTG | ACT | CCA | TTT | CTG | GCA | GCA | GCC | TGG | AGC |

| 101 | 102 | 103 | 104 |
|---|---|---|---|
| CTT | CAT | CCC | TAA |

GTC AAC ACC AGG AGAG CTT CTC
CCAAACTCCCCGTTCCTGCGTAGTCCGCTTTCTCT
TGCTGCCACATTCTAAAGGCTTGATATTTTCCAAA
TGGATCCTGTTGGGAAA ⋯ 3'

FIG. 1

| | | | | | | | | | |
|---|---|---|---|---|---|---|---|---|---|
| −25 | −24 | −23 | −22 | −21 | −20 | −19 | −18 | −17 | −16 |
| Met | Gly | Ile | Gln | Gly | Gly | Ser | Val | Leu | Phe |
| −15 | −14 | −13 | −12 | −11 | −10 | −9 | −8 | −7 | −6 |
| Gly | Leu | Leu | Leu | Val | Leu | Ala | Val | Phe | Cys |
| −5 | −4 | −3 | −2 | −1 | 1 | 2 | 3 | 4 | 5 |
| His | Ser | Gly | His | Ser | Leu | Gln | Cys | Tyr | Asn |
| 6 | 7 | 8 | 9 | 10 | 11 | 12 | 13 | 14 | 15 |
| Cys | Pro | Asn | Pro | Thr | Ala | Asp | Cys | Lys | Thr |
| 16 | 17 | 18 | 19 | 20 | 21 | 22 | 23 | 24 | 25 |
| Ala | Val | Asn | Cys | Ser | Ser | Asp | Phe | Asp | Ala |
| 26 | 27 | 28 | 29 | 30 | 31 | 32 | 33 | 34 | 35 |
| Cys | Leu | Ile | Thr | Lys | Ala | Gly | Leu | Gln | Val |
| 36 | 37 | 38 | 39 | 40 | 41 | 42 | 43 | 44 | 45 |
| Tyr | Asn | Lys | Cys | Trp | Lys | Phe | Glu | His | Cys |
| 46 | 47 | 48 | 49 | 50 | 51 | 52 | 53 | 54 | 55 |
| Asn | Phe | Asn | Asp | Val | Thr | Thr | Arg | Leu | Arg |
| 56 | 57 | 58 | 59 | 60 | 61 | 62 | 63 | 64 | 65 |
| Glu | Asn | Glu | Leu | Thr | Tyr | Tyr | Cys | Cys | Lys |
| 66 | 67 | 68 | 69 | 70 | 71 | 72 | 73 | 74 | 75 |
| Lys | Asp | Leu | Cys | Asn | Phe | Asn | Glu | Gln | Leu |
| 76 | 77 | 78 | 79 | 80 | 81 | 82 | 83 | 84 | 85 |
| Glu | Asn | Gly | Gly | Thr | Ser | Leu | Ser | Glu | Lys |
| 86 | 87 | 88 | 89 | 90 | 91 | 92 | 93 | 94 | 95 |
| Thr | Val | Leu | Leu | Leu | Val | Thr | Pro | Phe | Leu |
| 96 | 97 | 98 | 99 | 100 | 101 | 102 | 103 | | |
| Ala | Ala | Ala | Trp | Ser | Leu | His | Pro | | |

FUSION PROTEIN BETWEEN HUMAN MACIF AND A HETEROLOGOUS PI ANCHOR DOMAIN

This application is a continuation of application Ser. No. 08/021,724 filed Feb. 22, 1993, now abandoned, which is in turn a division of application Ser. No. 07/510,610, filed Apr. 18, 1990, now abandoned.

FIELD OF THE INVENTION

This invention relates to genes coding for a protein having human MACIF (membrane attack complex inhibition factor) activity, expression vectors with the genes respectively inserted therein, cells transformed with the expression vectors, and proteins having human MACIF activity. The term "protein having human MACIF activity" includes, within the meaning thereof, a group of proteins which regulate the complement system in the final stage of complement activation and inhibit damaging of human cells and tissues as a result of membrane attack complex formation.

BACKGROUND OF THE INVENTION

The present inventors previously succeeded in isolating a naturally occurring human MACIF, a so-far unknown protein regulating the complement system, in pure form from the human normal erythrocyte membrane (Japanese Patent Application No. 63-310642). They found that the human MACIF inhibits the activation of the late complement components or, in other words, inhibits hemolysis resulting from human MAC formation and, in this respect, the human MACIF is distinguished from and superior to the known complement-regulating substances that inhibit the activation of the early complement components, and that the naturally occurring human MACIF has the following N-terminal amino acid sequence:

```
  1    2    3    4    5    6    7    8    9   10
Leu—Gln—Cys—Tyr—Asn—Cys—Pro—Asn—Pro—Thr—
```

Furthermore, they found that this naturally occurring human MACIF is a glycoprotein having a molecular weight of 18,000±1,000 (as determined by SDS-polyacrylamide gel electrophoresis) with a phosphatidylinositol anchor (hereinafter abbreviated as "PI-anchor") at the C terminus.

For further studying of the above-mentioned protein having human MACIF activity and for developing the practical use of the protein as a drug, it is essential to obtain the protein in a pure and homogeneous form, and in sufficiently large quantities. For this purpose, application of the recombinant DNA technology appears to be the most effective means. However, the gene required for the means has not been isolated as yet.

Accordingly, an object of the invention is to provide a gene coding for a protein having human MACIF activity.

Another object of the invention is to provide a replicable expression vector capable of expressing the gene coding for a protein having human MACIF activity.

A further object of the invention is to provide a microorganism or cells transformed with the expression vector.

A still further object is to provide a genetically engineered protein having human MACIF activity.

SUMMARY OF THE INVENTION

The present invention provides genes respectively coding for polypeptides having human MACIF activity in which an amino acid sequence is represented by the following general formula (I):

```
  1    2    3    4    5    6    7    8    9   10           (I)
X—Leu  Gln  Cys  Tyr  Asn  Cys  Pro  Asn  Pro  Thr
 11   12   13   14   15   16   17   18   19   20
  Ala  Asp  Cys  Lys  Thr  Ala  Val  Asn  Cys  Ser
 21   22   23   24   25   26   27   28   29   30
  Ser  Asp  Phe  Asp  Ala  Cys  Leu  Ile  Thr  Lys
 31   32   33   34   35   36   37   38   39   40
  Ala  Gly  Leu  Gln  Val  Tyr  Asn  Lys  Cys  Trp
 41   42   43   44   45   46   47   48   49   50
  Lys  Phe  Glu  His  Cys  Asn  Phe  Asn  Asp  Val
 51   52   53   54   55   56   58   58   59   60
  Thr  Thr  Arg  Leu  Arg  Glu  Asn  Glu  Leu  Thr
 61   62   63   64   65   66   67   68   69   70
  Tyr  Tyr  Cys  Cys  Lys  Lys  Asp  Leu  Cys  Asn—Y
```

In the above formula, X and Y are defined as follows:

X is H,
Met, or the amino acid sequence:
Met Gly Ile Gln Gly Gly Ser Val Leu Phe Gly Leu Leu Leu Val Leu Ala Val Phe Cys His Ser Gly His Ser;

Y is OH,
the amino acid sequence:

```
 71   72   73   74   75   76   77   78   79   80
 Phe  Asn  Glu  Gln  Leu  Glu  Asn  Gly  Gly  Thr
 81   82   83   84   85   86   87   88   89   90
 Ser  Leu  Ser  Glu  Lys  Thr  Val  Leu  Leu  Leu
 91   92   93   94   95   96   97   98   99  100
 Val  Thr  Pro  Phe  Leu  Ala  Ala  Ala  Trp  Ser
101  102  103
 Leu  His  Pro,
``` or an amino acid sequence derived from this amino acid sequence by deleting therefrom one to thirty-two amino acid residues from the C terminus thereof.

The present invention further provides expression vectors respectively containing the genes mentioned above, microorganisms or cells transformed with the vectors, and genetically engineered proteins expressed in the microorganisms or cells and having human MACIF activity.

BRIEF DESCRIPTION OF THE DRAWINGS

FIG. 1 illustrates the gene isolated from human leukocytes and coding for an amino acid sequence including the naturally occurring human MACIF.

FIG. 2 illustrates an amino acid sequence deduced from the nucleotide sequence of the gene as shown in FIG. 1.

DETAILED DESCRIPTION OF THE INVENTION

Figure 3:
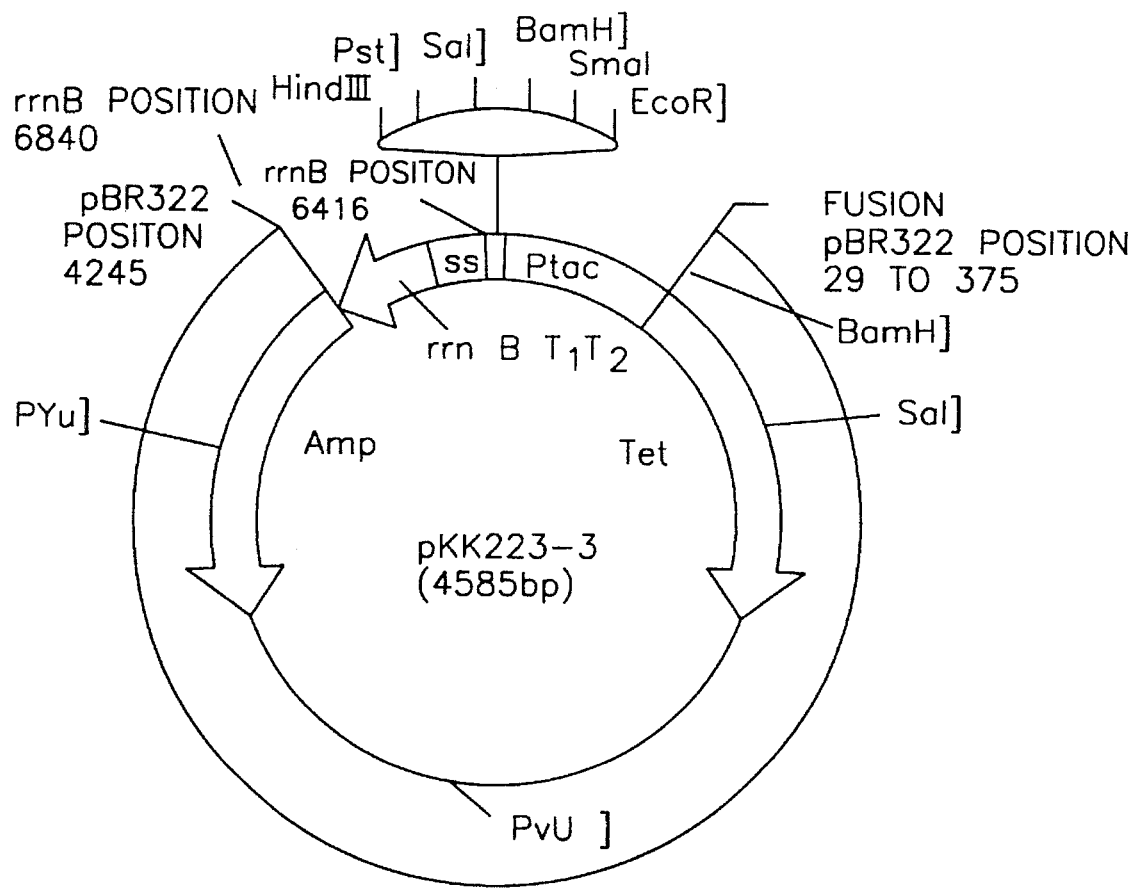
FIG. 3 illustrates the whole structure of an expression vector, pKK223-3, for use in *Escherichia coli.*

An example of the genes isolated from human leukocytes by the present inventors is the gene defined by the DNA sequence shown in FIG. 1. This gene contains a gene sequence coding for the amino acid sequence of that protein which exhibits physiological activities of naturally occurring human MACIF and, in addition, a gene coding for a naturally occurring human MACIF precursor amino acid sequence (inclusive of a secretory signal peptide and a PI anchor-attachment signal amino acid sequence, among others).

The secretory signal peptide-encoding gene is a gene coding for a peptide necessary for the protein having human MACIF activity which is produced in host cells to be released from the cell, while the PI anchor-attachment signal amino acid sequence-encoding gene is a gene coding for a hydrophobic amino acid sequence portion necessary for the attachment of the PI anchor to the protein having human MACIF activity.

Based on C-terminal analysis of a purified form of the naturally occurring human MACIF, the present inventors found that, in the naturally occurring human MACIF, the PI anchor is attached to the 76th amino acid (glutamic acid) residue of the amino acid sequence shown in FIG. 2. The PI anchor has a skeletal structure composed of phospho-ethanolamine, glycan and phosphatidylinositol (PI). The amino group of phospho-ethanolamine is attached to the carboxyl group of the C-terminal amino acid residue of peptides, and the fatty acid side chains of the PI is bound to the cell membrane. In this way, the PI-anchor serves as an anchor for binding peptides to the cell membrane. It was found that, in the amino acid sequence shown in FIG. 2, the sequence from the methionine residue at position −25 to the serine residue at position −1 is the secretory signal sequence and that the sequence from the asparagine residue at position 77 to the proline residue at position 103 is the PI anchor-attachment signal sequence. Thus, the amino acid sequence comprising the 1st to 76th amino acid residues constitutes a peptide core of naturally occurring human MACIF. In this specification, the term "human MACIF" means any protein essentially composed of the peptide comprising the first amino acid (leucine) residue to the 76th amino acid (glutamic acid) residue and the PI anchor attached to the C terminus of the peptide. This human MACIF may have a sugar chain of various kinds of structures depending on the host cells used for phenotypic expression or depending on culturing conditions of cells used therein. Human MACIF with a sugar chain of any structure as well as human MACIF without any sugar chain falls within the scope of the human MACIF according to the present invention.

For practical use as a drug having physiological activities of human MACIF, a protein is not required to have all the constituent elements of the above-mentioned human MACIF. It may be lacking in the PI anchor, or it may partially differ in amino acid sequence from human MACIF, provided that it has human MACIF activity. Thus, the desired proteins according to the present invention also include proteins having human MACIF-like physiological activities but differing from the very human MACIF in that a part of the amino acid sequence of human MACIF is missing in them or replaced with some other amino acid sequence, in that some amino acid sequence is added to or inserted in them, in that they have no PI anchor and/or in that they have no carbohydrate chain or differ in the kind of carbohydrate. In this specification, these objective proteins are referred to as "modified human MACIF proteins".

The genes provided by the present invention include genes coding for the above-mentioned human MACIF and modified human MACIF proteins. As typical examples of the modified human MACIF protein-encoding genes, there may be mentioned a gene coding for the amino acid sequence from the 1st amino acid residue (Leu) to the 70th amino acid residue (Asn) of the above-mentioned amino acid sequence of formula (I), a gene coding for the amino acid sequence from the 1st to the 75th amino acid residue (Leu) of the sequence of formula (I), a gene coding for the amino acid sequence from the 1st to the 77th amino acid residue (Asn) of the sequence of formula (I), a gene coding for the amino acid sequence from the 1st to the 82nd amino acid residue (Leu) of the sequence of formula (I) and a gene coding for the amino acid sequence from the 1st to the 86th amino acid residue (Thr) of the sequence of formula (I). In addition, mention may be made also of a gene coding for the amino acid sequence from the 1st to the 103rd amino acid residue (Pro) of the sequence of formula (I). When higher animal cells are used as host cells for its expression, this gene gives human MACIF with the PI anchor attached to the 76th amino acid residue (Glu), when expressed in bacteria, for instance, the gene gives a modified human MACIF protein comprising a peptide up to the 103rd amino acid residue (Pro); the PI anchor attachment does not occur in that case. Therefore, for convenience sake, such gene is included in the category of modified protein-encoding genes. Furthermore, a gene coding for the amino acid sequence up to the 76th amino acid residue (Glu) which constitutes the peptide core of human MACIF, when expressed on a vector, gives a soluble human MACIF polypeptide portion having no PI anchor. Such gene may also be included in the category of modified protein-encoding genes as defined above. In addition to those genes specifically mentioned above, genes coding for the amino acid sequence from the 1st up to the 71st to 85th amino acid residue can produce proteins having human MACIF activity and therefore are included among the genes according to the invention.

The genes according to the invention can be prepared by various methods. For example, a suitable method comprises isolating a clone containing cDNA coding for human MACIF from a cDNA library prepared from mRNA obtained from human MACIF-producing cells and isolating the MACIF cDNA from the thus-isolated clone. Another method comprises chemically synthesizing nucleic acids in the conventional manner, for example by the phosphoamidite method [Hunkapiller, M. et al., Nature, 310, 105–111 (1984)], based on the genetic information encoding human MACIF as disclosed herein. A combination of the above two methods may be mentioned as a further example. In the following, the method mentioned above that makes use of mRNA is described in further detail.

Oligonucleotide probe preparation

An oligodeoxyribonucleotide probe is prepared which is complementary to mRNA coding for the N-terminal amino acid sequence of purified, naturally occurring human MACIF isolated from human erythrocytes, for example, by chemical synthesis by the phosphoamidite method using a commercial DNA synthesizer (e.g., Applied Biosystems model 380A DNA synthesizer).

cDNA library preparation (1) Preparation of raw material cells:

Human cells of any kind in which the human MACIF according to the invention can be expressed may be used as the material for human MACIF mRNA in the practice of the invention. Advantageous as such cells from the high mRNA content viewpoint are human peripheral blood-derived leukocytic cells, human lymphocytic cells and other tissue cells as well as appropriate cell lines established therefrom.

Human peripheral blood-derived leukocytes and lymphocytes can be isolated from a normal human-derived buffy coat by density gradient centrifugation [Bøyum, A., Scandinavian Journal of Clinical Laboratory Investigations, 21, Supplement 97, 77–89 (1968)] using dextran or Ficoll-Hypaque, for instance. Tissue cells can be prepared from a tissue homogenate or the like in the conventional manner.

As the established human cell lines, there may be mentioned, for example, human erythroblastic leukemia cell lines (e.g., K562), human B cell leukemia cell lines (e.g., Raji), human T cell leukemia cell lines (e.g., MT-2), human monocytic leukemia cell lines (e.g., U937, HL60) and other tissue cancer cell lines (e.g., Bowes melanoma). The cell lines to be used are not limited to these, however. Such cell lines are readily available from the Salk Institute Cell Bank (California, U.S.A.) and other similar institutions. The cells are cultured in the manner of stationary culture, spinner culture or roller bottle culture, for instance, using an appropriate animal cell culture medium, e.g., commercially available RPMI 1640 medium [Moore, G. E. et al., Journal of American Medical Association, 199, 519–524 (1967)].

In some instances, stimulation of cells during cultivation can result in intracellular expression of human MACIF mRNA in increased amounts. The use of an immune complex as the stimulant is advantageous. As the stimulant, there may be further mentioned lectins [e.g., concanavalin A (ConA), phytohemagglutinin (PHA)], various antigens, phorbol esters [in particular 12-O-tetradecanoylphorbol-13-acetate (TPA)] and physiological stimulatory factors (e.g., interleukins, interferons, colony stimulating factors), among others. These may be used in combination of two or three of them.

(2) mRNA extraction:

An RNA fraction containing human MACIF-encoding mRNA can be extracted from cells of any of the kinds mentioned above in the conventional manner. Thus, for instance, the cells are partially or completely disrupted and/or solubilized by means of a guanidine thiocyanate solution or an appropriate detergent (e.g., SDS, NP-40, Triton X-100, deoxycholic acid) or by a physical means such as homogenization or hemolysis. Chromosomal DNA is then subjected, to a certain extent, to the shearing action of a mixer (e.g., Polytron) or a syringe, followed by separation of a nucleic acid fraction from proteins. Particularly useful for this fractionation procedure is the technique of extraction with phenol and chloroform or cesium chloride density gradient ultracentrifugation [Chirgwin, J. M. et al., Biochemisty, 18, 5294–5299 (1979); Maniatis, T. et al., Molecular Cloning, A Laboratory Manual, Cold Spring Harbor Laboratory, (1982)], among others.

In the above-mentioned extraction procedure, an RNAase inhibitor, for example, heparin, polyvinyl sulfate, diethyl pyrocarbonate or a vanadium complex, may be used as an additive for preventing RNA degradation due to RNase.

Isolation and purification of mRNA from the RNA obtained by the above extraction procedure can be effected, for example, by using an adsorption column of, for example, oligo-dT-cellulose (Collaborative Research) or poly-U-Sepharose (Pharmacia), or in a batchwise manner.

The thus-obtained mRNA is a mixture of mRNAs coding for a variety of proteins. Therefore, it may be purified and concentrated with respect to the desired mRNA that corresponds to human MACIF prior to cDNA library preparation. This purification and concentration can be performed as follows. Thus, the mRNA obtained in the above manner is fractionated by sucrose density gradient centrifugation, for instance, and the resulting fractions are tested for the presence of the desired human MACIF mRNA by dot plot hybridization, for instance.

(3) cDNA Library preparation:

The purified mRNA obtained in the above manner is generally unstable. Therefore, the mRNA is converted (reverse transcribed) to a stable complementary DNA (cDNA) and connected to a microorganism-derived replicon, enabling amplification of the desired gene. The in vitro mRNA conversion can be generally carried out by the Okayama-Berg method [Okayama, H. and Berg. P., Molecular and Cellular Biology, 2, 161–170 (1982)].

Thus, oligo-dT is used as a primer, which may be free oligo-dT or in the form already attached to a vector primer, and a single-stranded cDNA complementary to the mRNA is synthesized using the mRNA as a template and using reverse transcriptase in the presence of dNTPs (dATP, dGTP, dCTP and dTTP). The next step depends on whether the oligo dT is used in the free form or in the form attached to a vector primer.

In the former case, the template mRNA is removed by decomposing it by treatment with an alkali, for instance, and then a double-stranded DNA is synthesized in the presence of reverse transcriptase or DNA polymerase I with the single-stranded DNA as a template. The resultant double-stranded DNA is then treated at both ends thereof with SI nuclease and, after addition of an appropriate linker DNA or a plurality of bases whose combination allows annealing to the respective ends, inserted into an appropriate vector, for example, an EK system plasmid vector (either of the stringent type or of the relaxed type), or a λgt phage vector.

In the latter case, the mRNA to serve as a template is allowed to remain as it is, and the opened circular plasmid with the same linkers as mentioned above added thereto is annealed with a linker DNA (frequently a DNA fragment containing a region autonomously replicable in cells and an mRNA transcription promoter region) to give a closed circular form. Then, the mRNA is replaced with a DNA chain in the presence of dNTPs and in the simultaneous presence of RNase H and DNA polymerase I to give a complete plasmid DNA.

The cDNA-containing plasmid vector obtained in the above manner can be introduced into a host for transformation thereof. Typical as the host is *Escherichia coli*. However, the host is not limited to this but may be, for example, *Bacillus subtilis* or *Saccharomyces cerevisiae*.

The host can be transformed by introducing the DNA mentioned above by various methods commonly used in the art, for example, by collecting cells mainly at the logarithmic growth phase, treating them with calcium chloride for rendering them ready for spontaneous DNA uptake and allowing them to take up the plasmid. In the procedure mentioned above, magnesium chloride or rubidium chloride may be allowed to additionally coexist in the transformation system for further improvement of the transformation efficiency, as is generally known in the art. It is also possible to convert host cells to the spheroplast or protoplast state prior to transformation.

Cloning of cDNA

A strain carrying the desired human MACIF cDNA can be detected from among the transformants obtained in the above manner by various methods, for example, the methods mentioned below.

(1) Screening using a synthetic oligonucleotide probe:

In cases where a part of the amino acid sequence of the desired protein is known, as in the case of the present invention, oligonucleotides corresponding to the amino acid sequence portion is synthesized and this is used as a probe (after labeling with $^{32}$P or $^{35}$S) for detecting and selecting a positive strain by hybridization with transformant-derived DNAs denatured and immobilized on a nitrocellulose filter. The oligonucleotide may have a base sequence derived based on the codon frequency data or a combination of presumable base sequences. In the latter case, the number of probes can be reduced by incorporating inosine thereinto.

(2) Selection using an antibody to human MACIF:

The cDNA is inserted in advance into a vector capable of protein expression in transformants, protein production is allowed to proceed therein, and the anti-human MACIF antibody and a second antibody to the antibody are used to detect and select a desired human MACIF producer cell.

(3) Screening by producing human MACIF in other animal cells:

Transformant strains are cultured for gene amplification. The genes are used to transfect animal cells (using a plasmid capable of autonomously replicating and containing an RNA transcription promoter region or a plasmid capable of integrating into animal cell chromosomes). The proteins encoded by the genes are allowed to be produced and the culture supernatants or cell extracts are assayed for human MACIF activity. Alternatively, a transformant strain carrying the desired cDNA coding for human MACIF is selected from among transformant strains by detecting the human MACIF produced therein by using an antibody to human MACIF.

Confirmation of human MACIF cDNA

The gene according to the present invention obtained by the use of mRNA as a starting material can be confirmed to be a gene properly coding for human MACIF by using an appropriate translation system. Most commonly used is the method developed by Krieg et al. [Krieg, P. A. et al., *Nucleic Acids Research*, 12, 7057–7070 (1984)], which comprises synthesizing a large quantity of mRNA in vitro using a potent promoter and an RNA polymerase specific to the promoter, followed by translation of the mRNA into a protein using a simple translation system. Thus, in the above method, the cDNA of the present invention is inserted into an appropriate plasmid downstream from a potent promoter, such as the SP6 promoter, T7 promoter or T3 promoter, (in the case of the use of mRNA as a starting material, the vector containing these promoters can be previously used in the library preparation), and the resulting plasmid is purified and then cleaved at an appropriate restriction enzyme cleavage site occurring downstream from the human MACIF cDNA which occurs downstream from such promoter. The resulting double-stranded DNA is transcribed to mRNA in vitro using a polymerase specific to the promoter used, such as SP6 polymerase, T7 polymerase or T3 polymerase, respectively. The thus-transcribed mRNA is then translated into a protein by using a cell-free protein synthesizing system, such as a rabbit reticulocyte lysate or wheat germ lysate, or by the method comprising injecting the mRNA into *Xenopus laevis* oocytes. That the gene correctly coding for human MACIF has been obtained can be confirmed by assaying for MACIF activity of the translation product protein, or by an immunological method using an antibody specific to human MACIF.

Gene sequence determination

The nucleotide sequence of the thus-obtained gene of the present invention can be determined, for example, by the dideoxy method using a plasmid vector [Chen, E. Y., DNA, R, 165–170 (1985)] or by the 7-DEAZA method [Mizusawa, S. et al., *Nucleic Acids Research*, 14, 1319–1324 (1986)]. The thus-obtained gene for naturally occurring human MACIF (derived from human leukocytes) is shown in FIG. 1.

While the method of preparing the gene of the present invention as detailedly described above goes via mRNA, the gene coding for human MACIF can also be prepared by chemical synthesis based on the nucleotide sequence disclosed herein. A typical example of the method of chemical synthesis is the phosphoamidite method.

Construction of expression vectors (1) Selection of the host-vector system:

The whole length of the coding region of the thus-obtained human MACIF gene can be expressed using a eukaryote or prokaryote as the host. The vector to be integrated into such host cells can be constructed in an appropriate manner depending on the host cells.

As the prokaryote host, there may be mentioned *Escherichia coli* strains [e.g., *E. coli* K12 294 (ATCC 31446), *E. coli* B, *E. coli* X1776 (ATCC 31537), *E. coli* C600, *E. coli* W3110 (F-, λ-, prototrophic; ATCC 27375)], Bacillus strains [e.g., *B. subtilis*], enteric bacteria other than *E. coli*, for example, *Salmonella typhimurium* and *Serratia marcescens*, and Pseudomonas strains.

Usable as the vector for such microorganism hosts is an expression vector which contains the gene of the present invention with a promoter and an SD base sequence [Shine, J. et al., Proc. Natl. Acad. Sci. U.S.A., 71, 1342–1346 (1974)] located upstream of the gene, together with ATG necessary for protein synthesis initiation. Generally, pBR322, pBR327 and the like are vectors suited for use in *Escherichia coli* and other microbial strains.

Usable as the promoter are, for example, the tryptophan promoter, PL promoter, lac promoter, 1pp promoter and β-lactamase promoter.

As typical examples of the marker gene, there may be mentioned the ampicillin resistance gene and tetracycline resistance gene.

Yeasts are generally used as the eukaryotic microorganism. In particular, yeasts belonging to the genus Saccharomyces can be used advantageously. A typical example of the expression vector for use in yeasts and other eukaryotic microorganisms is YRp7.

Useful examples of the promoter which the expression vector for expression in yeasts should have are the 3-phosphoglycerate kinase, enolase, glyceraldehyde- 3-phosphate dehydrogenase or hexokinase promoters.

The trp1 gene, for example, can be used as the marker gene.

The origin of replication, termination codon and other DNA sequences which serve to regulate transcription and translation in yeast cells may be ordinary DNA sequences known to be suited for use in yeast cells.

When cultured higher animal cells are used as the host, they may be rhesus monkey kidney cells, mosquito larva cells, African green monkey kidney cells, mouse fetus fibroblasts, Chinese hamster ovary (CHO) cells, a dihydrofolate reductase-deficient strain thereof [Urlaub, G. et al., Proc. Natl. Acad. Sci., U.S.A., 77, 4216–4220 (1980)], human cervical epithelial cells, human fetus kidney cells, moth ovary cells, human myeloma cells or mouse fibroblasts, for instance.

The vector generally contains functional sequences for expression of the DNA of the present invention in host cells, for example, the origin of replication, promoter located upstream from the DNA of the present invention, ribosome binding site, polyadenylation site and transcription termination sequence.

Preferred examples of the promoter are the adenovirus 2 major late promoter, SV40 early promoter, SV40 late promoter, eukaryotic gene-derived promoters (e.g., estrogen-inducible chicken egg albumin gene, interferon gene, glucocorticoid-inducible tyrosine aminotransferase gene, thymidine kinase gene, adenovirus major early and late genes, phosphoglycerate kinase gene, α-factor gene).

The origin of replication may be derived from adenovirus, SV40, bovine papilloma virus (BPV), vesicular stomatitis virus (VSV), or any of vectors derived from these.

The neomycin resistance gene, and methotrexate resistant dihydrofolate reductase (DHFR) gene, among others, can be used as the marker gene in this case.

The examples of the host, vector and constituent elements thereof that have been described hereinabove as usable for the expression of the human MACIF cDNA and modified human MACIF protein cDNAs are by no means limitative of the scope of the present invention.

(2) Construction of human MACIF expression vectors:

Since, as mentioned hereinbefore, human MACIF is a protein having the PI anchor at the C terminus of the polypeptide chain, the host cells for its expression must be selected from among cells having the PI anchor synthesizing mechanism. Such mechanism is known to be distributed among a wide variety of organisms from prokaryotes, yeasts and myxomycetes to insects and mammals. As examples of the host cells that can be expected to allow production of a polypeptide having the PI anchor at the C terminus thereof in the state of art, there may be mentioned CHO cells [Caras, I. W. et al., *Nature*, 322, 545–549 (1987)], COS cells [Caras, I. W. et al., *Science*, 243, 1196–1198 (1989)] and R1.1 thymoma cells [Waneck, G. L. et al., *Science*, 241, 697–699 (1988)], but the host cells are not limited thereto. In the following, a method of constructing a human MACIF cDNA expression vector particularly suited for the expression in Chinese hamster ovary cells (CHO cells) as host cells is described in detail.

A human MACIF cDNA-containing clone, PGEM352-3, is isolated from human monocyte cDNA library constructed with commercially available plasmid vector PGEM4 (Promega) mainly used for in vitro transcription. The plasmid pGEM352-3, is cleaved with the restriction enzymes SacI and HincII, followed by agarose gel electrophoresis to give a SacI/HincII DNA fragment of about 425 base pairs. This fragment is rendered blunt-ended by treatment with mung bean nuclease.

Figure 4:
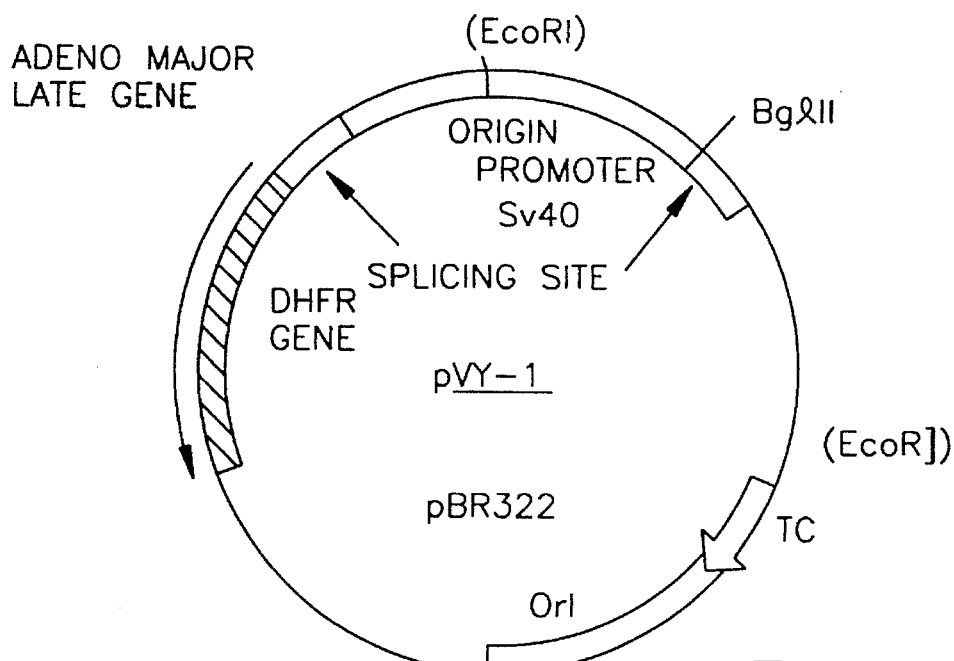
FIG. 4 illustrates the whole structure of an expression vector, pVY1, for use in CHO cells.

On the other hand, the main body vector for constructing an expression vector for use in CHO cells is prepared by cleaving pVY-1 (shown in FIG. 4) with BglII, followed by treatment with mung bean nuclease to render the resulting BglII ends blunt-ended. This main body vector and the blunt-ended SacI/HincII DNA fragment mentioned above are joined together using T4 DNA ligase, and the ligation mixture is used to transform *Escherichia coli* HB101. Plasmids are prepared from the thus-obtained transformants by the alkali method and subjected to restriction enzyme analysis. In this way, a plasmid capable of expressing the gene is selected out.

The thus-prepared expression plasmid is transformed into methotrexate (Mtx)-susceptible CHO cells by the calcium phosphate method. Since transformants acquire Mtx resistance, a strain capable of expressing the polypeptide can be selected from among the Mtx-resistant strains. When the gene is expressed in CHO cells, the expression product polypeptide is deprived of the signal peptide, with or without further processing, to give mainly a protein having the PI anchor attached to the C terminus.

A vector for the expression of human MACIF having the phosphatidylinositol anchor at the C terminus can be constructed also by the known technology mentioned hereinbelow using a modification of the above gene modified in the portion which codes for the hydrophobic signal sequence for PI anchor attachment beginning with the 77th amino acid residue (Asn) of the polypeptide of formula (I).

From the teaching of Caras et al. [Caras, I. W. et al., *Science*, 238, 1280–1283 (1987)], it is well known in the art that the phosphatidylinositol anchor can be attached to the C terminus of any desired protein when a hybrid DNA is constructed by adding a DNA coding for the hydrophobic signal sequence for PI anchor attachment at the C terminus of a precursor for a known PI-anchored protein to the 3' terminus of a DNA coding for a desired protein and then expressed using a recombinant vector such as mentioned hereinbefore. The hydrophobic signal sequence for PI anchor attachment may be any of those known PI anchor attachment signal sequences for precursors for PI-anchored proteins that are described in a review by Ferguson et al. [Ferguson, M. A. et al., *Annual Review of Biochemistry*, 57, 285–320 (1988)] and elsewhere.

According to Caras et al. [Caras, I. W. et al., *Science*, 243, 1196–1198 (1989)], it is possible that the N-terminal secretory signal sequence of human growth hormone or a random hydrophobic peptide sequence can be used as a polypeptide sequence usable as a signal for PI anchor attachment at the C terminus. This suggests that human MACIF with the PI anchor attached thereto can be expressed as well by using a hybrid gene produced by connecting such a hydrophobic sequence as mentioned above to the 3' side of a DNA sequence coding for the portion of human MACIF which ends in the 76th amino acid residue (Glu).

In view of the above, it is evident that the gene sequence to be used in constructing an expression vector for the production of human MACIF with the PI anchor attached to the C terminus thereof is not limited to the DNA sequence shown in FIG. 1.

The human MACIF polypeptide with the PI anchor attached to the C terminus thereof is generally expressed on the cell membrane of the transformant. Therefore, the recombinant human MACIF on the cell surface can be detected in the conventional manner by reacting the transformant cells with an anti-human MACIF antibody and a fluorescence-labeled second antibody, followed by flow cytometry or analysis on a fluorescence-activated cell sorter (FACS). If no human MACIF can be detected on the cell surface any more by the above method after treatment of the transformant cells with phosphatidylinositol-specific phospholipase C (PI-PLC), it can conversely be verified that the recombinant MACIF obtained in the above manner has the PI anchor attached thereto.

Such a method as mentioned above makes it possible to confirm that a recombinant human MACIF is produced in cells transformed in the above manner.

(3) Construction of expression vectors for modified human MACIF protein:

A method of constructing vectors for the expression of modified human MACIF proteins is described in the following.

These are recombinant vectors capable of expressing proteins substantially equivalent in physiological activities to human MACIF. They are vectors comprising a DNA sequence derived from the DNA base sequence shown in FIG. 1 by deleting any portion thereof, for example, such that the expression product lacks in a part of its N-terminal or C-terminal amino acid sequence, or by modifying any portion thereof such that the corresponding amino acid sequence be replaced by some other amino acid sequence, or by adding an appropriate sequence such that some amino acid sequence be added to the expression product, together with those constituent elements necessary for expression in a variety of host systems mentioned in the above section (1). More specifically, these expression vectors include a series of recombinant vectors in which a gene coding for a polypeptide defined by the amino acid sequence of formula (I) is effectively connected to and placed under the control of a regulatory DNA sequences capable of causing expression of the polypeptide.

When bacterial cells, which have no PI anchor synthesizing mechanism, are used as the host for expression of the above-mentioned expression vectors, the expression product is always a polypeptide having no PI anchor.

When mammalian cells are used as the host, the PI anchor addition is controlled in a complicated manner. It is generally known that when PI anchor attachment to the C terminus of a polypeptide takes place, elimination of a specific hydrophobic C-terminal polypeptide portion (PI-anchor attachment signal sequence) from a precursor for the polypeptide precedes modification with the PI anchor. In the case of human MACIF, the polypeptide from the 77th amino acid residue (Asn) to the 103rd amino acid residue (Pro) acts as a signal for PI anchor attachment. However, the respective modified protein genes inserted in the expression vectors for those modified proteins mentioned above which are composed of amino acid residues No. 1 to No. 70 to 86 are lacking in the portion of DNA which codes for a part or the whole of the PI anchor attachment signal sequence. It is known that deletion of a gene fragment coding for a part of the hydrophobic attachment signal sequence from a gene coding for a protein precursor to which a PI anchor is to be added results in production of a soluble protein [Berger, J. et al., *Journal of Biological Chemistry*, 263, 10016–10021 (1988)]. Therefore, these genes of the present invention which code for the modified proteins can possibly be used as genes for producing soluble modified human MACIF proteins.

Among the vectors for the expression of these modified proteins, a vector for the expression in *Escherichia coli* of a protein comprising those amino acid residues up to the 103rd one shown in FIG. 2, vectors for the expression in *Escherichia coli* and in mammalian cells of modified MACIF proteins comprising those amino acid residues up to the 86th, 77th and 70th, respectively, are described in more detail in the following together with methods of their construction and expression.

(a) Expression in *Escherichia coli* of a protein comprising the 1st to 103rd amino acid residues:

The plasmid pGEM352-3 is cleaved with the restriction enzymes PstI and HincII and a PstI/HincII DNA fragment of about 310 base pairs is isolated and purified by agarose gel electrophoresis.

A synthetic DNA of the formula (II):

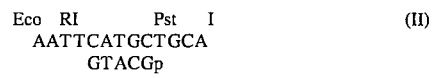

is phosphorylated at the PstI cleavage site is joined to the PstI/HincII fragment prepared as above-mentioned at the PstI cleavage site thereof using T4 DNA ligase. The thus-produced, synthetic DNA-joined DNA fragment (now EcoRI/HincII fragment) is isolated and purified by agarose gel electrophoresis.

Separately, a vector main body for constructing an expression vector for use in *Escherichia coli* is prepared, for example, by cleaving pKK223-3 shown in FIG. 3 with EcoRI and SmaI. This vector and the above-mentioned EcoRI/HincII DNA fragment are ligated together using T4 DNA ligase and the ligation mixture is used to transform *E. coli* K12JM109 by the calcium chloride method. Plasmids are isolated from transformants by the alkaline method and analyzed using restriction enzymes. In this way, a transformant harboring the desired plasmid with the EcoRI/HincII DNA fragment inserted therein can be selected.

The desired polypeptide can be expressed and produced by cultivating the transformant obtained as described above in an appropriate medium (e.g., L medium containing 100 mM isopropyl-β-D-thiogalactopyranoside). The polypeptide expressed has methionine residue at the N terminus thereof. The expression product also includes the polypeptide species which has no N-terminal methionine as a result of elimination by the action of an enzyme occurring in *Escherichia coli* cells and capable of eliminating the N-terminal methionine residue.

(b) Expression of a protein comprising the 1st to 86th amino acid residues:

When *Escherichia coli* is used as the host, pGEM352-3 is cleaved with AvaII. Separately, a synthetic DNA of the formula (III):

```
Ava II
pGACCTGTGAACTTTAACGAACAGCTTGAAAATGGTGGGACA
    GACACATTGAAATTGCTTGTCGAACTTTTACCACCCTGT

Hind III
TCCTTATCAGAGAAAACATGA
AGGAATAGTCTCTTTTGTACTTCGA
```
(III)

is phosphorylatd at the AvaII cleavage site. The cleavage product and phosphorylated synthetic DNA are ligated together using T4 DNA ligase. The ligation product is then cleaved with PstI and ligated with the synthetic DNA of formula (II) phosphorylated at the PstI cleavage site, using T4 DNA ligase. The thus-produced ligation product (now EcoRI/Hind III fragment) from the synthetic DNA and DNA fragment is isolated and purified by agarose gel electrophoresis.

The thus-prepared EcoRI/HindIII DNA fragment is ligated with an EcoRI/HindIII fragment of pKK223-3. A recombinant *Escherichia coli* strain, which allows expression of a polypeptide comprising the 1st to 86th amino acid residues, can be obtained using the ligation product and proceeding in the same manner as described above.

For polypeptide expression in CHO cells, pGEM352-3 is cleaved with AvaII and then ligated with the synthetic DNA of formula (III), as in the case of expression in *Escherichia coli* cells. The ligation product is then cleaved with SacI and a DNA fragment of about 375 base pairs is isolated and purified by agarose gel electrophoresis. This DNA fragment is rendered blunt-ended by treatment with mung bean nuclease. The resulting DNA fragment is inserted into pVY1 cleaved with BglII and rendered blunt-ended to give an expression plasmid. Transformation of CHO cells with the expression plasmid gives CHO cells capable of expressing and producing a polypeptide comprising the 1st to 86th amino acid residues.

(c) Expression of proteins comprising the 1st to 77th amino acid residues and the 1st to 70th amino acid residues, respectively:

For causing expression of the gene coding for the 1st to 77th amino acid residues or the 1st to 70th amino acid residues in *Escherichia coli* or CHO cells, essentially the same procedure as mentioned above can be followed except that, in the plasmid preparation step, the synthetic DNA to be joined to pGEM352-3 after cleavage of the latter with AvaII is a synthetic DNA of the formula (IV):

```
    Ava II                                  Hind III
pGACCTGTGAACTTTAACGAACAGCTTGAAAATTGA
    GACACATTGAAATTGCTTGTCGAACTTTTAACTTCGA,
```
(IV)

when the polypeptide comprising the 1st to the 77th amino acid residues is to be expressed, or a synthetic DNA of the formula (V):

```
    Ava II              Hind III
pGACCTGTGTAACTGA
    GACACATTGACTTCGA,
```
(V)

when the polypeptide comprising the 1st to the 70th amino acid residues is to be expressed.

The subsequent steps, the corresponding genes and recombinant vectors for the expression of the genes can be obtained by proceeding in the same manner as described above in (b).

Transformation

Introduction of the thus-obtained expression vectors containing the human MACIF cDNA or modified human MACIF protein cDNA into desired host cells, namely transformation of the cells with the vectors, can be effected using these techniques that are used generally.

Each expression vector plasmid can be prepared from the host used for gene construction (e.g. *E. coli* HB101) by a method in general use, for example, alkaline bacteriolysis. The vector plasmid prepared is used to transform the host. The transformation can be effected by the method of Hanahan [Hanahan, D., *Journal of Molecular Biology*, 166, 557–580 (1983)], for instance, when bacterial cells are used as the host, or by the calcium phosphate method [van der Eb, A. J. et al., *Methods in Enzymology*, 65, 826–839 (1980), Academic Press], for instance, when mammalian cells are used as the host.

Cultivation and purification

The transformant obtained in the above manner can be grown in the conventional manner and cultivation thereof results in production and accumulation of a biologically active human MACIF or modified human MACIF proteins. The medium for the cultivation can suitably be selected from among various conventional media depending on the host cells employed. For instance, when the above-mentioned CHO cells are used as the host, MEM-α medium if necessary supplemented with a blood component such as fetal calf serum (FCS), may be used.

The site of expression for the production of the recombinant human MACIF or recombinant modified human MACIF proteins in the transformant differs depending on the amino acid sequence encoded by the cDNA selected, the kind of vectors, that of the host cells and the combination of these. Thus, the recombinant human MACIF or modifications thereof can be produced on the cell membrane, within the cell or in the cell culture supernatant. The human MACIF or modified human MACIF proteins produced in transformed cells can be isolated and purified therefrom by various separation techniques [e.g., Japanese Biochemical Society (ed.), Biochemical Data Book II, 1st edition, 1st printing, page 1175, Tokyo Kagaku Dojin (1980)] based on the physical and chemical properties thereof.

To be concrete, the techniques include, among others, treatment with an ordinary protein-precipitating agent, ultrafiltration, molecular sieve chromatography (gel filtration), adsorption chromatography, ion exchange chromatography, affinity chromatography, high-performance liquid chromatography (HPLC), other liquid chromatographic techniques, dialysis, and combinations of these. To be more concrete, the technique to be used may vary depending on the site of expression of the recombinant protein.

Recombinant proteins produced in the culture supernatant can be isolated and purified in the following manner.

First, the desired substance is partially purified from the culture supernatant in advance. This partial purification is realized, for example, by treatment with an agent for salting out, such as ammonium sulfate, sodium sulfate or sodium phosphate, and/or ultrafiltration treatment using a dialyzing membrane, flat membrane or hollow fiber membrane. The procedure and conditions of each of these treatments may be the same as those generally employed in the art. The roughly purified product obtained in the above manner is subjected to adsorption chromatography, affinity chromatography, gel filtration, ion exchange chromatography, reversed-phase chromatography or the like or a combination of these, and a fraction showing human MACIF activity is recovered. In this manner, the desired substance can be isolated in a pure and homogeneous form.

A recombinant protein produced on the cell membrane may have a PI anchor and, therefore, may be bound to the cell membrane via the anchor. Such membrane-bound recombinant protein can be purified by disrupting the cell membrane by treatment with an appropriate detergent (e.g. NP-40, Triton X-100, octylglycoside) and then proceeding in the same manner as described above. Alternatively, a recombinant protein bound to the cell membrane via the PI anchor can be solubilized by an appropriate treatment for PI anchor cleavage. As the means of PI anchor cleavage, there may be mentioned, for example, cleavage with phosphatidylinositol-specific phospholipase C (PI-PLC) and cleavage with phosphatidylinositol-specific phospholipase D (PI-PLD). The recombinant protein solubilized by the above treatment is released into the cell culture supernatant and therefore can be purified in the same manner as described above.

A recombinant protein produced in the cell can be purified by disrupting the cell membrane by treatment with an appropriate detergent, as in the case of membrane-bound recombinant proteins, to thereby cause release of the recombinant protein into the solution phase and then proceeding in the same manner as mentioned above.

The activity of the thus-purified recombinant human MACIF, soluble recombinant human MACIF or recombinant modified human MACIF proteins can be identified, for example, by measuring of reactive lysis [Thompson, R. A. et al., *Journal of Experimental Medicine*, 131, 629–641 (1970) and Lachmann, P. J. et al., *Journal of Experimental Medicine*, 131, 643–657 (1970)] inhibiting activity assay.

In the foregoing, the genes according to the present invention, the vectors for the expression of the genes and the transformed microorganisms and cells capable of allowing the expression of the genes as well as the methods for their preparation have been described. As a result of the present invention, the DNA sequence of the human MACIF gene has been determined for the first time and at the same time genes coding for modified human MACIF proteins practically useful as drugs have been provided. Thus, it is now possible to produce a pure and homogeneous grade of human MACIF or a modification thereof in large quantities by using the recombinant DNA technology.

Human MACIF and modified human MACIF proteins are of the human origin. Therefore, they have no antigenicity and their toxicity is low. They can prevent cells and tissues from being damaged as a result of MAC formation in the last stage of complement activation. Thus, they can be used advantageously as therapeutic agents for various diseases, in particular diseases resulting from the absence or reduced level of a complement-regulating component(s) and all diseases classifiable under the category of type II or type III allergy.

Furthermore, not only in disease due to the absence or reduced level of one or more complement-regulating components, typically in paroxysmal nocturnal hemoglobinuria (PNH), but also in various inflammatory or autoimmune diseases accompanied by cell and/or tissue damage, a qualitative or quantitative abnormality in human MACIF may possibly be observed. Therefore, human MACIF and modified proteins derived therefrom, monoclonal or polyclonal antibodies specific to human MACIF or a modification thereof, human MACIF or modified human MACIF protein DNAs and, further, DNAs complementary to the human MACIF or modified human MACIF protein genes can be used in specific diagnosis of the above-mentioned diseases.

The dosage form of human MACIF or modified human MACIF proteins may vary depending on the diseases, symptoms and patient's conditions. Generally, however, non-oral dosage forms, such as injections, nasal preparations, suppositories and implants, are used for systemic administration, while intraarticular preparations and preparations to be implanted into affected sites, for instance, are used for local administration.

In preparing these dosage forms, compositions suited for the respective forms are used. In preparing injections, human MACIF or a modified human MACIF protein is dissolved in phosphate-buffered physiological saline or an aqueous dextrose solution, for instance, and, after addition of a stabilizer, a dispersant and/or the like, as necessary, distributed into ampules or lyophilized in vials. In the latter case, the preparation is reconstituted prior to use by dissolving in distilled water for injection or physiological saline.

The daily dose of MACIF for human adults is generally within the range of 100 µg to 5,000 mg, preferably within the range of 1 mg to 500 mg. Such daily dose is administered in a single dose or in divided doses.

Dosage form preparation example

A solution of 5 g of MACIF in 100 ml of physiological saline is subjected to aseptic filtration and then distributed in 2-ml portions into vials. Lyophilization gives a preparation for injection, each vial containing 100 mg of MACIF.

EXAMPLES (1) Determination of N-terminal and C-terminal amino acid sequences of a purified sample of naturally occurring human MACIF:

1) N-terminal amino acid sequence determination

A purified sample of naturally occurring human MACIF (18 kilodaltons) was reduced in the conventional manner with 2-mercaptoethanol in the presence of 8M urea, then S-carboxymethylated with iodoacetic acid, and analyzed for its N-terminal amino acid sequence using a gas phase protein sequencer (model 470A, Applied Biosystems, U.S.A.). The result was as follows:

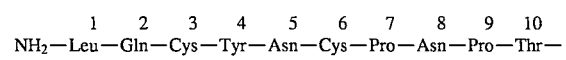

2) C-terminal amino acid sequence determination:

A 0.6 mg portion of the purified sample of naturally occurring human MACIF was reduced in the conventional manner with dithiothreitol in the presence of 6M guanidine hydrochloride and S-carboxymethylated with iodoacetic acid. The alkylation mixture was dialyzed against distilled water overnight at 4° C. and the dialyzate was concentrated to 0.5 ml using a centrifuge-type reduced-pressure concentrator. The whole carboxymethylated human MACIF solution was buffered by addition of 1M Tris hydrochloride buffer (pH 8.0). Then, a solution of 100 μg of Pronase (Calbiochem) in 20 μl of 50 mM Tris hydrochloride buffer was added to the solution, and the reaction was allowed to proceed at 37° C. for 22 hours.

A chloroform-methanol (1:1) mixture (0.5 ml) was added to the reaction mixture. After thorough shaking, the whole mixture was centrifuged, whereupon it separated into a transparent upper layer, a cloudy middle layer and a transparent lower layer. A portion of each layer was taken, hydrolyzed with 6N hydrochloric acid and analyzed in the conventional manner using a Picotag work station equipment (Waters, U.S.A.). Ethanolamine was detected in the middle layer. It was thus revealed that the middle layer contained a Pronase digestion fragment with a PI anchor attached at the C terminus. The middle layer (600 μl) containing the above PI anchor-attached C-terminal fragment was lyophilized, 1.2 ml of a water:n-butanol:1N hydrochloric acid (600:600:3) mixture was added and, after thorough shaking, the mixture was centrifuged. Hydrolysis was performed with 6N hydrochloric acid in the same manner as described above and analyzed using a Picotag work station equipment. Ethanolamine was detected in the butanol layer (upper layer). An equal volume of n-butanol-saturated 5 mM hydrochloric acid was added to the upper layer, the mixture was shaken and then centrifuged and the upper layer was separated. This extraction procedure with acidic butanol was repeated twice in all.

Half of the final n-butanol layer was subjected to amino acid sequence determination using the protein sequencer mentioned above.

As a result, the following sequence was found:

```
            72    73    74    75    76
   NH2 — Asn — Glu — Gln — Leu — Glu
``` this covers from the 72nd to the 76th amino acid residue in the sequence shown in FIG. 2. No amino acid residue was detected behind the 76th amino acid residue (Glu). The above facts indicated that erythrocyte-derived, naturally occurring human MACIF has the PI anchor attached to the Glu which is the 76th amino acid residue from the N terminus.

(2) Preparation of oligonucleotide probes for detecting cDNA clones coding for human MACIF:

Based on the amino acid sequence revealed in the above section (1), 15-mer and 17-mer mixed deoxyoligo-nucleotide probes complementary to the mRNA regions coding for amino acid residues Nos. +1 to +5 and +4 to +9, respectively, were chemically synthesized by the phosphoamidite method using a model 380A DNA synthesizer (Applied Biosystems) and labeled with $^{32}$P at the 5' end.

The 15-mer mixed probe (hereinafter referred to as "M1 probe") had the nucleotide sequences:

```
     5'-AATGTTACAATATTA-3'    (32 sequences) and
           C  C       G  G
```

-continued
```
     5'-GAAGTTACAATATTA-3'    (64 sequences)
           G  C  G  G  G
              T
              C
``` while the 17-mer mixed probe (hereinafter referred to as "M4 probe") had the nucleotide sequences

```
     5'-ATATTAACAGGATTAGG-3'   (64 sequences).
              G  G  G  G  G
                       T
                       C
```

(3) Preparation of a human monocyte cDNA library:

Recombinant plasmids were constructed by the Okayama-Berg method (vide supra) starting with mRNA derived from immune complex-stimulated human peripheral blood monocytes and the commercially available plasmid vector pGEM4 (Promega). The recombinant plasmids thus constructed had cDNA inserted between the KpnI cleavage site and SacI cleavage site of the multicloning sites occurring between the SP6 promoter region and T7 promoter region of pGEM4. The directionality of cDNA was such that the KpnI side (T7 promoter side) was on the 3' side of mRNA and the SacI side (SP6 promoter side) was on the 5' side of mRNA.

The recombinant plasmid mixture thus obtained was used to transform E. coli HB101 competent cells (Takara Shuzo) and a cDNA library comprising about 400,000 transformants was obtained.

(4) Cloning of human MACIF cDNA:

For isolating a transformant harboring a plasmid containing cDNA coding for human MACIF, the human monocyte cDNA library obtained as described in section (3) was subjected to colony hybridization using the synthetic oligonucleotide probes prepared as described in section (2) to detect clones hybridizing with both of M1 and M4 probes. A clone containing the longest cDNA (about 2,000 bp) was selected and, for the plasmid pGEM 352-3 isolated therefrom, a partial base sequence of the cDNA portion was determined by the dideoxy method (vide supra) using the plasmid vector and by the 7-DEAZA method (vide supra). The thus-determined cDNA sequence (about 500 bp) from the SP 6 promoter side (5' side of mRNA) of pGEM4 is shown in FIG. 1.

In the cDNA sequence of the pGEM352-3 clone, there is a sequence coding for the N-terminal ten amino acid residues of the purified human MACIF described in section (1), with the translation initiation codon ATG at a site corresponding to amino acid residue No. −25 upstream from the N terminus and the translation termination codon TAA at a site corresponding to the +104th amino acid residue downstream from the N terminus. The open reading frame thus formed codes for a protein comprising 128 amino acid residues. It is strongly suggested that the amino acid sequence corresponding to the region of −25 to −1 should be the so-called secretion signal sequence very rich in hydrophobicity.

(5) Expression of human MACIF cDNA in oocytes and confirmation of its biological activities:

The above-mentioned pGEM352-3 clone was used for in vitro transcription of its cDNA portion into mRNA utilizing the SP6 promoter occurring upstream from the cDNA in the presence of SP6 RNA polymerase. In parallel, the plasmid from a human IL-1α cDNA-containing clone was also used for in vitro transcription into mRNA. After microinjection of those mRNAs together with TE buffer (10 mM Tris-HCl, pH 8.0, 1 mM EDTA), a solvent therefor, into Xenopus laevis oocytes, in vitro translation was effected by incubating the oocytes at 20° C. for 48 hours in modified Barth's medium [Gurdon, J. B., *The Control of Gene Expression in Animal Development*, Oxford University Press, (1974)] (with 0.1 µCi/µl of $^{35}$S-Cys added in the case of immunoprecipitation). The oocytes were then disrupted by sonication in a solution containing 0.01% Nonidet P40 (NP40) (Sigma, U.S.A.) and centrifuged. The middle aqueous layer (hereinafter referred to as "translation product") was subjected to immunoprecipitation and activity measurement.

1) Reactivity of translation products with antibodies (immunoprecipitation):

Each translation product was reacted with rabbit anti-human MACIF polyclonal antibody or rabbit anti-human TNF polyclonal antibody, the antibody was bound to PAN-SORBIN (*Staphylococcus aureus* cells, Hoechst, West Germany), the binding mixture was centrifuged, the sediment was washed three times with binding buffer (Affi-gel Protein A MAPS-II kit, Bio-Rad, U.S.A.) and then centrifuged with 0.17M glycine hydrochloride (pH 3.0), and the supernatant was measured for $^{35}$S-Cys using a liquid scintillation counter (TRI-CARB 460, Packard, U.S.A.). It was revealed, as shown below in Table 1, that only the translation product obtained by submitting pGEM352-3 to the in vitro transcription/translation system can react specifically with the rabbit anti-human MACIF polyclonal antibody.

TABLE 1

| | $^{35}$S-Cys Radioactivity (cpm) | |
|---|---|---|
| RNA | Anti-Human MACIF | Anti-Human TNF |
| TE | 254 | 222 |
| | 235 | 208 |
| 352-3 | 1577 | 381 |
| | 1249 | 278 |
| IL1-α | 165 | 169 |
| | 218 | 410 |

2) Biological activity of translation products:

2-1) Partial purification on an anti-human MACIF antibody column

The above translation products were adsorbed each on an antibody column prepared by binding a purified mouse monoclonal anti-human MACIF antibody to activated Sepharose 4B (Pharmacia, Sweden). The column was then washed thoroughly with phosphate-buffered saline (PBS) containing 0.1% NP40 and with 2M aqueous solution of sodium chloride containing 0.1% NP40.

The translation product adsorbed on each antibody column was eluted with 3M aqueous solution of sodium thiocyanate containing 0.1% NP40. After buffer exchange for SGVB$^{2+}$ containing 0.01% NP40, the eluate was used for activity measurement. The SGVB$^{2+}$ buffer mentioned above has the following composition: 0.1% gelatin, 5 mM sodium barbiturate buffer (pH 7.4), 8.56% sucrose, 0.15 mM calcium chloride, 1 mM magnesium chloride.

2-2) Activity assay of translation products:

Human C5–C6 complex (stored frozen and thawed before use; $\overline{C5,6}'$) was prepared from human C5 and C6 by the method of Dessauer et al. [Dessauer, A. et al., *Acta Pathologica Microbiologica Scandinavia*, Section C, Supplement 284, 92, 75–81 (1984)] and admixed with a guinea pig erythrocyte suspension ($10^7$ cells/ml), and the mixture was incubated at 33° C. for 5 minutes. Then, after addition of C7, incubation was performed further for 15 minutes to give a guinea pig erythrocyte-human complement C5–7 complex (hereinafter referred to as "EC5-7 intermediate"). The EC5-7 intermediate suspension ($1.5\times10^8$/ml) was admixed with C8, C9 and a sample solution to make the total volume 1 ml ($1.5\times10^7$/ml). Incubation was carried out at 37° C. for 1 hour. In parallel, a control suspension prepared in the same manner but without addition of any sample solution was incubated simultaneously. The reaction mixture was centrifuged at 2,000×g for 5 minutes, the supernatant was measured for absorbance (at 414 nm) for hemolysis percentage calculation. Thus, the number of sites (Z) per erythrocyte was calculated by the method of Hammer et al. [Hammer, C. H. et al., *Journal of Biological Chemistry*, 256, 3995–4005 (1981)] and the ratio in percentage of the Z value to the Z value for the control was taken as an index of activity.

Figure 5:
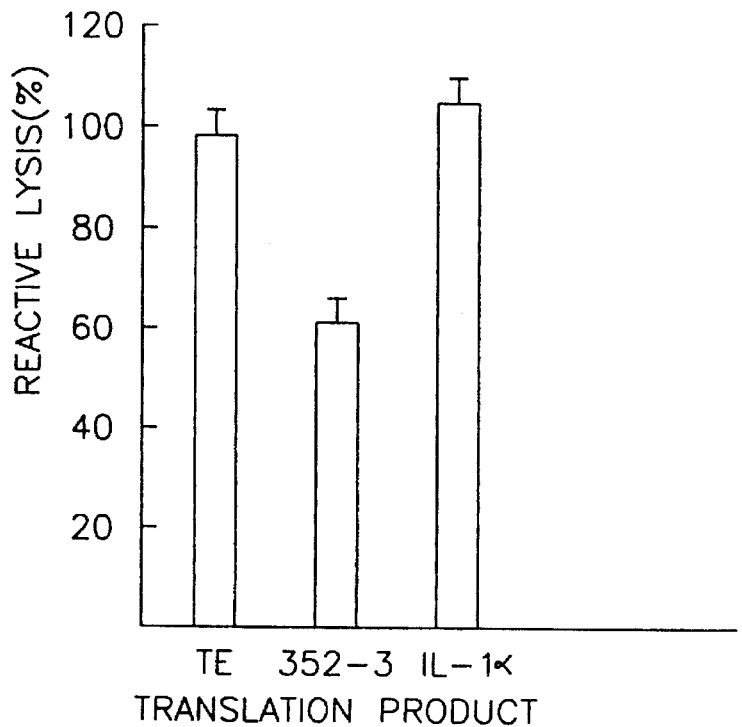
FIG. 5 illustrates the results of a test of some translation products for their antihemolytic activity in guinea pig erythrocytes.
Figure 6:
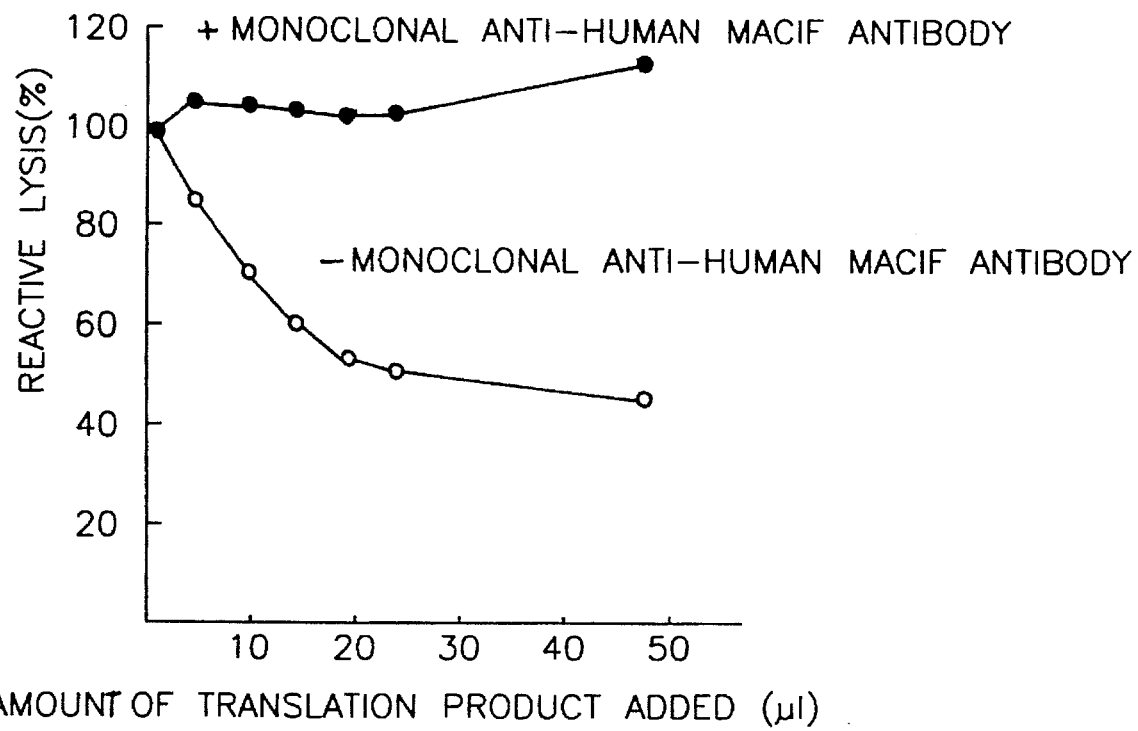
FIG. 6 illustrates the dose dependency of the inhibitory activity of a translation product in hemolysis of guinea pig erythrocytes and the result of neutralization of the product with an anti-human MACIF antibody.

No activity was observed with TE and IL1-α, each used as a control, while significant antihemolytic activity was observed with human MACIF (FIG. 5). This activity was dose-dependent and was completely neutralized with a mouse monoclonal antibody to human MACIF (FIG. 6).

It is therefore evident that the cDNA contained in the pGEM352-3 clone obtained in the above described (4) codes for human MACIF.

Figure 7:
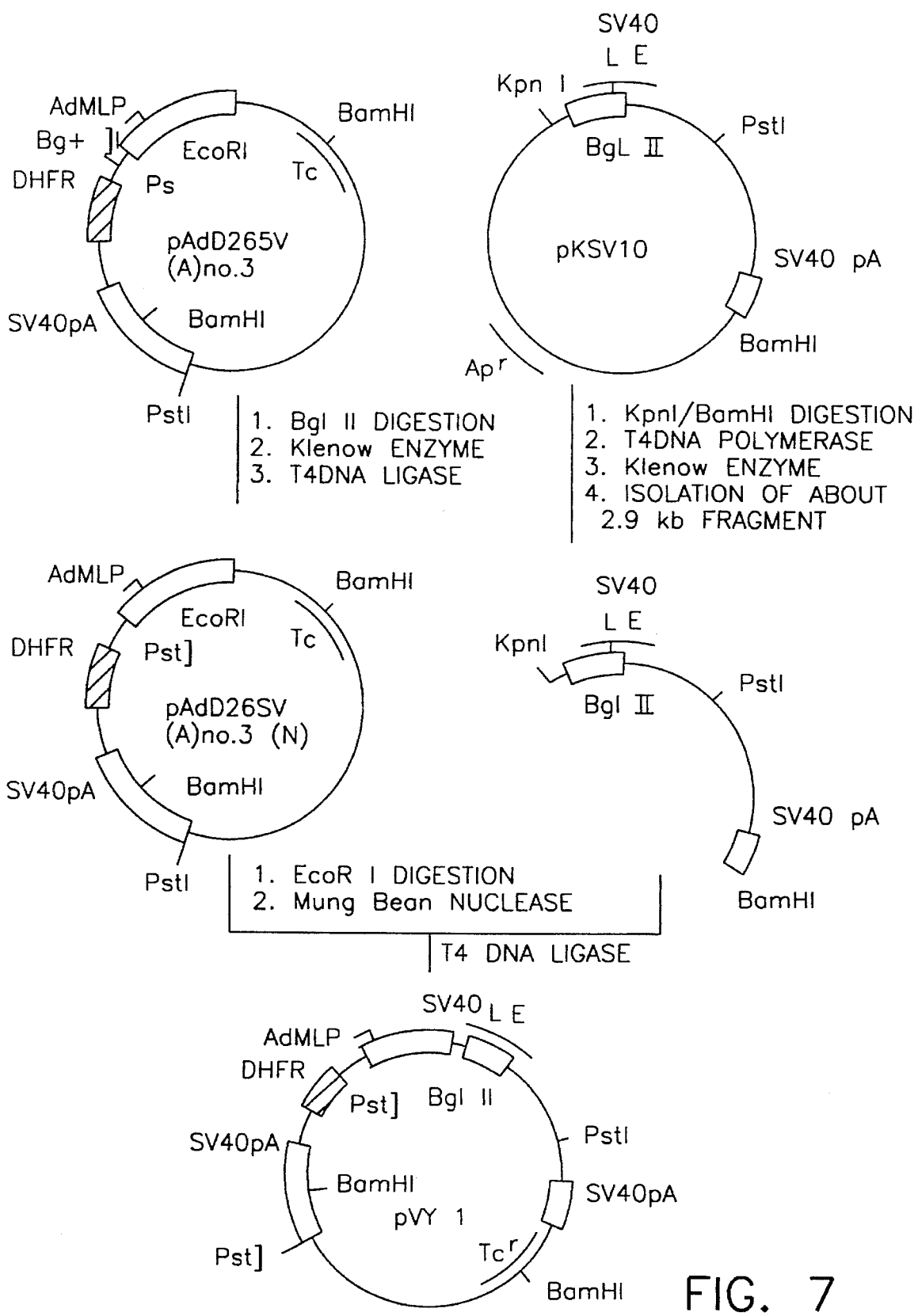
FIG. 7 illustrates a construction scheme for the expression vector pVY1.

(6) Construction of the expression vector pVY1:

The expression vector pVY1 was constructed as illustrated in FIG. 7.

1) The DNA of the vector pAdD26SV(A) No. 3 [obtained from Dr. H. Handa; made known by the paper: Kaufman, R. J. and Sharp, P. A., *Molecular and Cellular Biology*, 2, 1304–1319 (1982)] was first cleaved with BglII, followed by phenol-chloroform extraction and ethanol precipitation. The precipitate thus obtained was dissolved in sterile distilled water, rendered blunt-ended in the conventional manner using Klenow enzyme (Boehringer Mannheim), then subjected to phenol-chloroform extraction and ethanol precipitation, and dissolved in sterile distilled water. It was further self-ligated using a DNA ligation kit (Takara Shuzo). The ligation mixture was used to transform competent cells of *E. coli* HB101. Plasmid DNAs were obtained from tetracycline-resistant transformants. A portion of each of these DNAs was treated with BglII and electrophoresed on a 0.7% agarose gel. In this way, a clone having no BglII site any more, pAdD26SV(A) No. 3(N), was obtained.

The plasmid DNA was then digested with EcoRI, followed by phenol-chloroform extraction and ethanol precipitation. The precipitate was dissolved in sterile distilled water, and the EcoRI cleavage site was rendered blunt-ended using mung bean nuclease (Pharmacia), followed by phenol-chloroform extraction and ethanol precipitation. The precipitate thus obtained was dissolved in sterile distilled water.

2) The pKSV10 (Pharmacia) DNA was cleaved in the conventional manner with the restriction enzymes KpnI and BamHI and then rendered blunt-ended using T4 DNA polymerase (Takara Shuzo) and Klenow enzyme. After electrophoresis on a 0.7% agarose gel, the gel portion containing a fragment about 2.9 kbp in size was separated and the DNA was recovered by electroelution.

3) The DNA fragment obtained as described in the above 1) and the DNA fragment obtained as described in the above 2) were ligated together using a DNA ligation kit and the ligation mixture was used to transform competent cells of *E. coli* HB101.

Plasmid DNAs were prepared from tetracycline-resistant transformants by a conventional method. A part of each plasmid DNA was digested with PstI and the digest was subjected to 1.0% agarose gel electrophoresis. In this manner, the plasmid pVY1 giving bands at about 3.6 kbp, about 3.25 kbp and about 1.5 kbp was obtained.

(7) Expression of human MACIF cDNA in CHO cells:

1) Construction of a human MACIF cDNA expression vector:

The plasmid pGEM352-3 was cleaved with the restriction enzymes SacI and HincII and a SacI/HincII DNA fragment of about 425 base pairs was isolated and purified by agarose gel electrophoresis. This DNA fragment was rendered blunt-ended by treatment with mung bean nuclease.

pVY1 obtained as described in the above (6) was used as the expression vector for use in CHO cells. Thus, pVY1 was cleaved with BglII and treated with mung bean nuclease to render blunt the BglII cleavage end. The resulting blunt-ended DNA was ligated with the above-mentioned blunt-ended SacI/HincII DNA fragment using T4 DNA ligase and the ligation mixture was used to transform *E. coli* HB101 to give tetracycline-resistant transformants. Plasmids were prepared from them by the alkaline bacteriolytic method [Birnboim, H. C. and Dolly, J., *Nucleic Acids Research*, 7, 1513–1523 (1979)] and subjected to restriction enzyme analysis using PstI and so forth. In this way, a plasmid capable of allowing expression of the gene in question was selected out.

2) Confirmation of the expression of the human MACIF gene in CHO cells:

The expression plasmid constructed in the above manner was transfected into DHFR-deficient CHO cells [Urlaub, G. and Chasin, L. A., *Proc. Natl. Acad. Sci. U.S.A.*, 77, 4216–4220 (1980)] by the calcium phosphate method (vide supra). A transformant growing on a selective medium [MEM alpha (−), Gibco] was obtained.

Figure 8A:
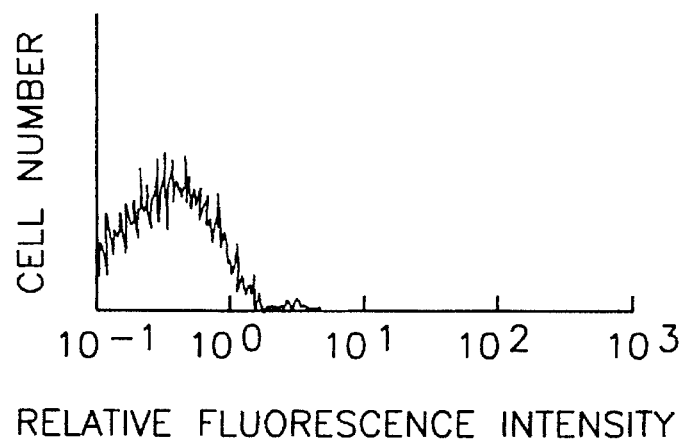
FIGS. 8a, 8b, 8c illustrates flow cytometric analysis of recombinant human MACIF expression in transformant CHO cells.
Figure 8B:
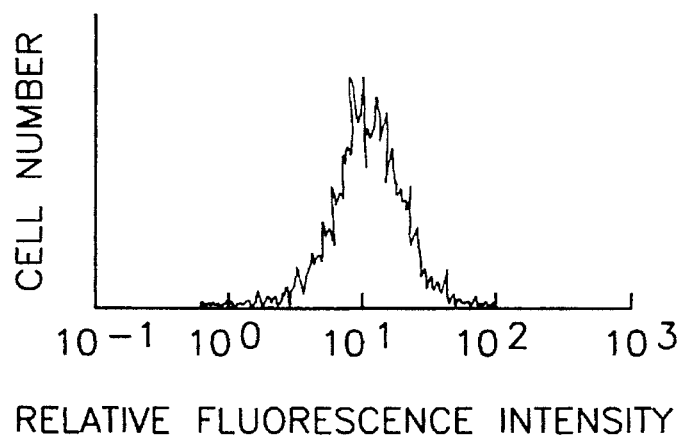

The transformant CHO cell strain was grown on the selective medium and $5 \times 10^5$ cells thereof were washed three times with phosphate-buffered saline (PBS) and suspended in 500 µl of the culture supernatant obtained by cultivating hybridoma cells capable of producing a monoclonal antibody (IgG1) to human MACIF. The reaction was allowed to proceed for 1 hour with ice cooling. In parallel, a control run was carried out in the same manner using the culture supernatant resulting from cultivation of hybridoma cells capable of producing a monoclonal antibody (IgG1) to human protein S. After reaction, the cells were washed three times with PBS containing 2% fetal calf serum and 0.1% sodium azide (hereinafter referred to as "washing solution"), and then allowed to react, in a concentration of $1 \times 10^6$ cells/ml, with FITC (fluorescein isothiocyanate)-labeled anti-mouse immunoglobulin (Amersham Japan) 50-fold diluted with the same washing solution, for 30 minutes with ice cooling. The cells were then washed three times with the washing solution and analyzed with a flow cytometer (EPICS PROFILE, Coulter, U.S.A.). When the anti-human MACIF antibody was used, the fluorescence intensity was found shifted to a higher level, as shown in FIG. 8a and FIG. 8b, indicating the binding of the anti-human MACIF antibody to the cells. It was thus confirmed that the transformed CHO cells had expressed human MACIF.

Figure 8C:
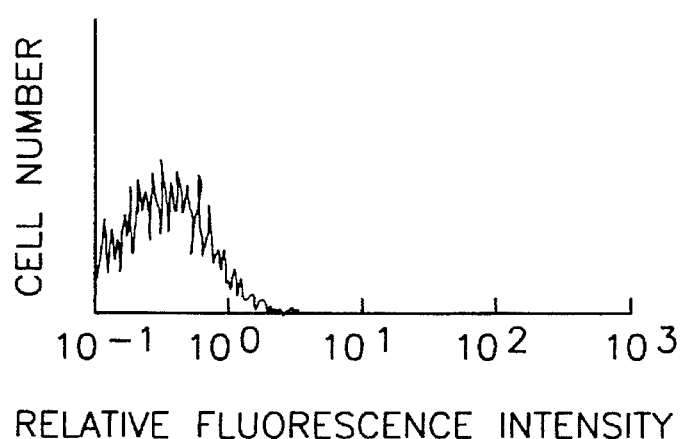

Furthermore, the transformed CHO cells were washed with PBS, then incubated with phosphatidylinositol-specific phospholipase C (PI-PLC, Funakoshi, Sapporo Breweries) at 37° C. for 30 minutes, washed three times with the washing solution and subjected to fluorescent staining with the anti-human MACIF monoclonal antibody and with the FITC-labelled anti-mouse immunoglobulin in the same manner as above. As seen in FIG. 8c, the fluorescence intensity lowered to the control level upon treatment with PI-PLC, indicating the release of human MACIF expressed in the transformed CHO cells from the membrane upon treatment with PI-PLC. It was thus confirmed that the human MACIF expressed on the transformed CHO cells had been expressed on the cell membrane as a PI anchored protein susceptible to cleavage with PI-PLC.

3) Biological activity evaluation of the protein resulting from the expression of human MACIF cDNA in CHO cells:

For confirming the biological activity feature of human MACIF expressed in the transformed CHO cells mentioned above, transformant CHO cell were prepared in large quantities by cultivation thereof, washed with PBS and solubilized by treating the cells overnight at 4° C. with NP40 at 2% in PBS containing various proteinase inhibitors [1 mM benzamidine, 2 mM phenylmethylsulfonyl fluoride (PMSF), 2 mM ethylenediaminetetraacetic acid (EDTA) and 2 mM ethylene glycol bis(β-aminoethyl ether)-N,N,N',N'-tetraacetic acid (EGTA), all obtained from Sigma]. Each supernatant obtained by centrifugation (12,000 rpm, 30 minutes) was partially purified by the method mentioned hereinabove under (5)-2-1) using an anti-human MACIF monoclonal antibody column and then subjected to biological activity evaluation.

Figure 9:
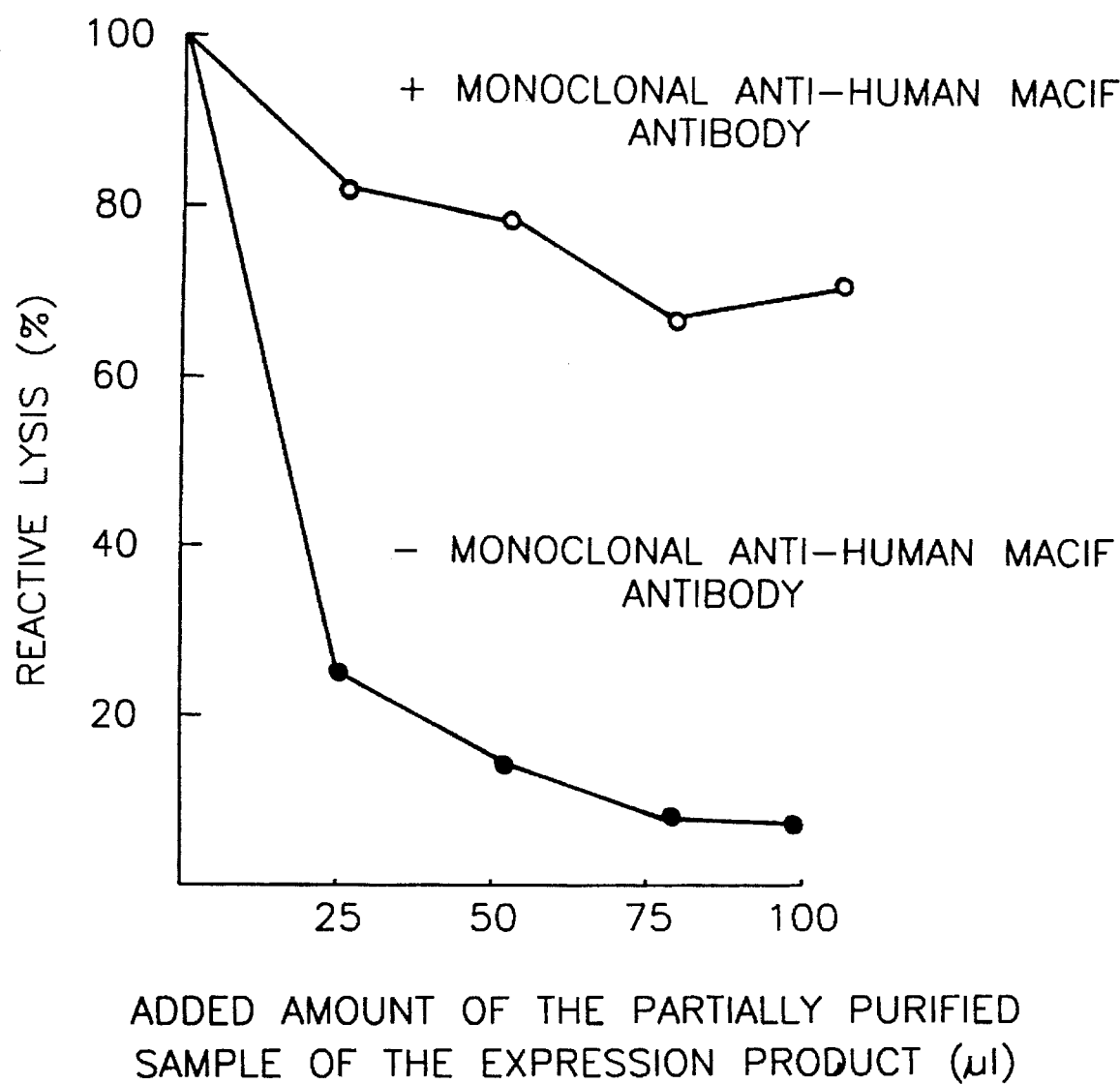
FIG. 9 illustrates the dose dependency of the inhibitory activity in hemolysis of guinea pig erythrocytes, of recombinant human MACIF expressed in transfomant CHO cells and the result of neutralization thereof with an anti-human MACIF antibody.

The MAC formation inhibiting activity (reactive lysis inhibiting activity) of the human MACIF partially purified from the transformant CHO cells was evaluated by the method described under (5)-2-2). As shown in FIG. 9, the human MACIF expressed in the CHO cells exhibited MAC formation inhibiting activity, which was dose-dependent. This inhibitory activity was neutralized by a mouse monoclonal antibody to human erythrocyte-derived MACIF.

The above results clearly indicate that the human MACIF expressed in CHO cells is equivalent in activity to human erythrocyte-derived MACIF.

(8) Expression in *Escherichia coli* of a gene coding for a modified human MACIF protein 1) Construction of a modified human MACIF protein expression vector and expression in *Escherichia coli*

1-1) Preparation of a vector for expression in *Escherichia coli*

Figure 10:
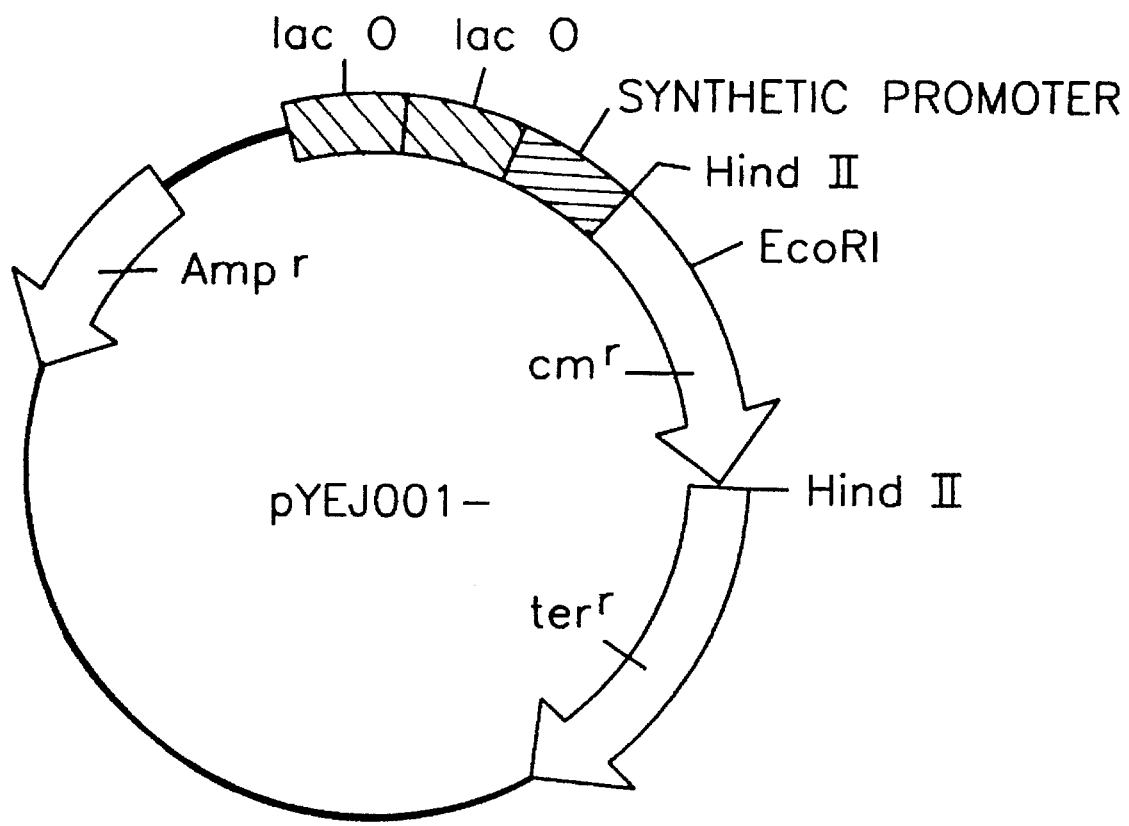
FIG. 10 illustrates the whole structure of a vector, pTEJ001, for expression in *Escherichia coli*.

The vector pYEJ001 (Pharmacia; FIG. 10) for expression in *Escherichia coli* was cleaved with the restriction enzyme HindIII, and the vector main body containing the origin of replication and the promoter for expression of the gene in question was isolated and purified by agarose gel electrophoresis and then treated with alkaline phosphatase for terminal phosphate group elimination.

The DNA fragment to be inserted into the vector, inclusive of the SD sequence, modified human MACIF protein gene and transcription terminator, was prepared in the following manner.

1-2) Preparation of an insert DNA fragment for the expression of a modified human MACIF protein (E103) comprising the peptide sequence up to the 103rd amino acid residue pGEM352-3 was cleaved with the restriction enzymes PstI, HincII and BamHI and a DNA fragment of about 310 base pairs was isolated and purified by agarose gel electrophoresis. Separately, the synthetic DNAs B and C shown by the following formula (VI) were terminally phosphorylated using polynucleotide kinase.

```
         SD BOX                                          (VI)
5'-AGCTT ACACAT AAGGAGAT CGAATT CATGCTGCA-3'      A
    3'-AT GT GT ATT CCT CT AGCTT AAGT ACG-5'       B
  HindIII                              PstI
```

TRP A TERM
5'-GGGAGCCCGCCTAATGAGCGGGCTTTTTTTA-3'       C
3'-CCCTCGGGCGGATTACTCGCCCGAAAAAAATTCGA-5'   D
                                      HindIII The synthetic DNA A (shown above) and the phosphorylated B were heated to 90° C. and then slowly cooled down to 16° C. for annealing. The phosphorylated C and the synthetic DNA D (shown above) were treated in the same manner for annealing. The two DNA annealing products and the previously prepared DNA of about 310 base pairs were ligated together using T4 DNA ligase, and a DNA fragment of about 375 base pairs containing the region coding for the modified human MACIF protein E103 was isolated and purified by agarose gel electrophoresis.

1-3) Preparation of an insert DNA fragment for the expression of a modified human MACIF protein (E86) comprising the peptide sequence up to the 86th amino acid residue The previously prepared DNA fragment of about 310 base pairs was cleaved with the restriction enzyme MboII and a DNA fragment of about 250 base pairs was isolated and purified by agarose gel electrophoresis.

Separately, two (B and C) of the four synthetic DNAs of the formulas (VII):

SD BOX                                                      (VII)
5'-AGCTTACACATAAGGAGATCGAATTCATGCTGCA-3'           A
    3'-ATGTGTATTCCTCTAGCTTAAGTACG-5'                B
   HindIII                              PstI TRP A TERM
5'-AAACATGATCAAGCCCGCCTAATGAGCGGGCTTTTTTTA-3'      C
3'-TTTTGTACTAGTTCGGGCGGATTACTCGCCCGAAAAAAATTCGA-5' D
                                             HindIII were terminally phosphorylated using polynucleotide kinase. A and the phosphorylated B were heated to 90° C. and then gradually cooled to 16° C. for effecting annealing. The phosphorylated C and unphosphorylated D were treated in the same manner for annealing. The two annealing product DNAs and the previously prepared DNA fragment of about 250 base pairs were ligated together using T4 DNA ligase and a DNA fragment of about 325 base pairs containing the region coding for the modified MACIF protein E86 was isolated and purified by agarose gel electrophoresis.

1-4) Preparation of a vector for the expression of the modified human MACIF protein in *Escherichia coli* and transformation therewith:

The thus-prepared two DNA fragments were terminally phosphorylated using polynucleotide kinase and then ligated with the separately prepared vector main body using T4 DNA ligase. The ligation mixture was used to transform *E. coli* K12JM109. Plasmids were prepared from the transformants obtained by the alkaline method (vide supra) and analyzed using restriction enzymes (e.g. by cleavage with PstI), and a plasmid with the gene in question inserted therein in the direction enabling the gene to be expressed was selected out.

1-5) Expression and cultivation:

One volume of 2×YT medium (16 g of Bactotryptone, 10 g of yeast extract and 5 g of sodium chloride per liter) supplemented with 100 μg/ml of ampicillin was inoculated with 1/50 volume of a preculture of a recombinant *E. coli* strain allowing expression of the gene in question. Then, culture was shaken at 37° C. and the recombinant *E. coli* strain was grown until cell density had reached about $5 \times 10^7$/ml, and then isopropyl thiogalactopyranoside was added in a concentration of 2.5 mM. After further 16 hours of cultivation, cells were harvested.

The cells collected were suspended in PBS containing 2 mM EDTA, 2 mM EGTA, 1 mM benzamidine, 2 mM phenylmethylsulfonyl fluoride (PMSF) (all purchased from Sigma) and disrupted using a Manton-Gaulin homogenizer.

2) Purification of the protein resulting from the expression of the modified human MACIF protein gene in *Escherichia coli* and biological activity assay:

2-1) Purification:

The *Escherichia coli* cell disruption product prepared as described above was centrifuged (12,000 rpm, 30 minutes) and the sediment was stirred overnight at 4° C. in the presence of 6M guanidine hydrochloride for solubilization.

The remaining insoluble matter was removed by centrifugation under the same conditions as mentioned above. The expression product protein (E103 or E86) contained in the supernatant was reconstituted by treatment in the presence of oxidized-form and reduced-form glutathione (Sigma) according to the method of Winkler and Blaber [Winkler, M. E. and Blaber, M., *Biochemistry*, 256, 4041–4045 (1986)].

The reconstitution mixture was thoroughly dialyzed against 10 mM Tris buffer (pH 8.0) and then purified by application to Q-Sepharose (Pharmacia) preequilibrated with the same buffer.

Figure 11:
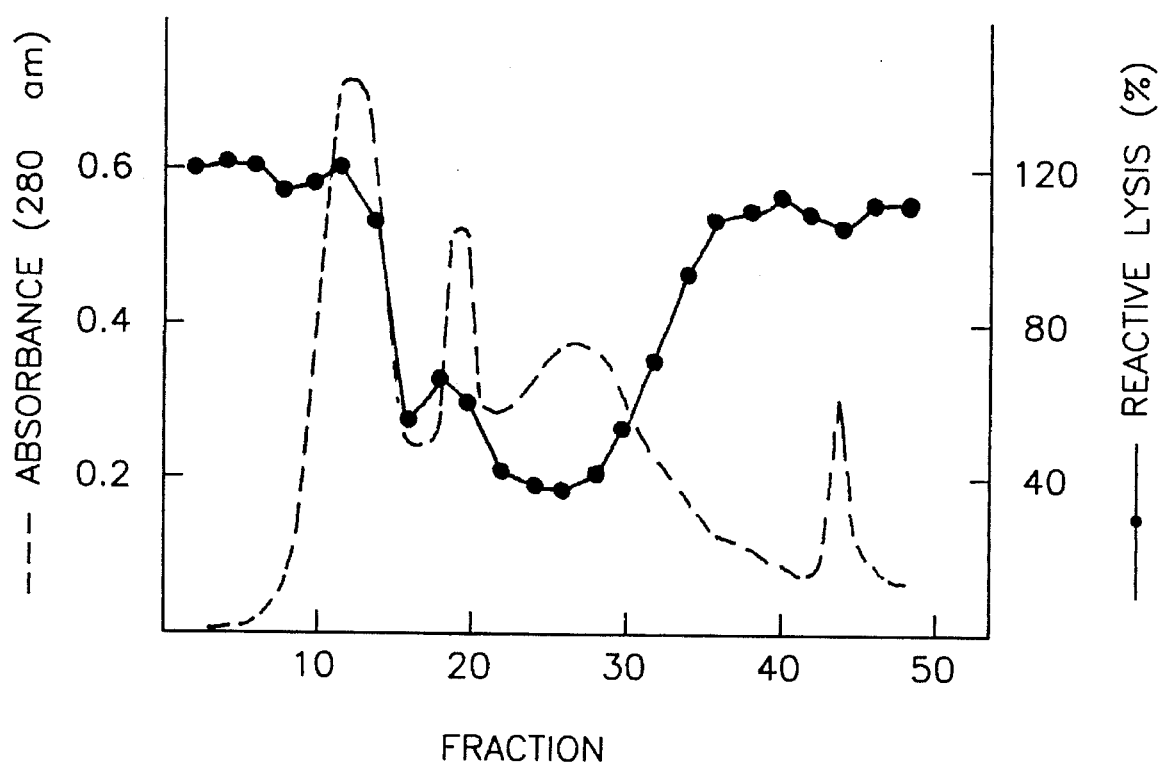
FIG. 11 illustrates the results of purification of a modified human MACIF protein (E103) expressed in *Escherichia coli* using Q-Sepharose.

2-2) Activity of the modified human MACIF protein (E103):

As shown in FIG. 11, the reactive lysis inhibiting activity data obtained by the method described in section (5)-2-2) showed two peaks. However, the second activity peak (around fraction No. 25) alone was partially neutralized by the anti-human MACIF monoclonal antibody.

Figure 12:
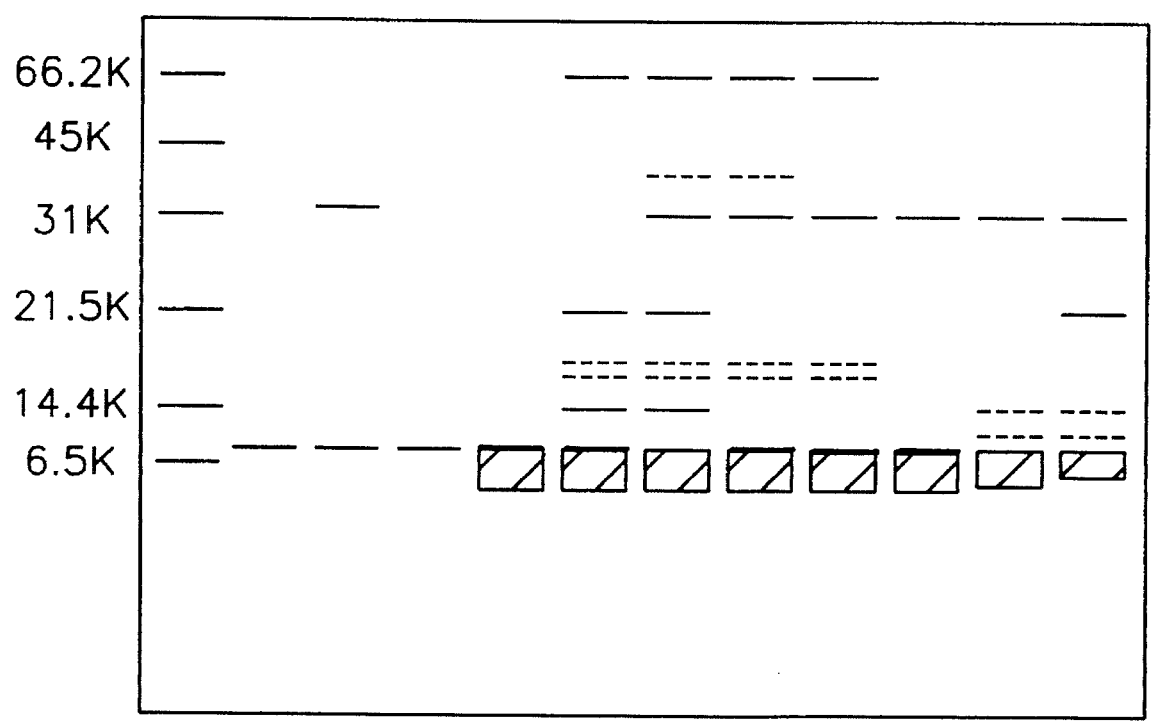
FIG. 12 illustrates the results of SDS-PAGE analysis of fractions obtained by purification of the modified human MACIF protein E103 expressed in *Escherichia coli* using Q-Sepharose.
Figure 13:
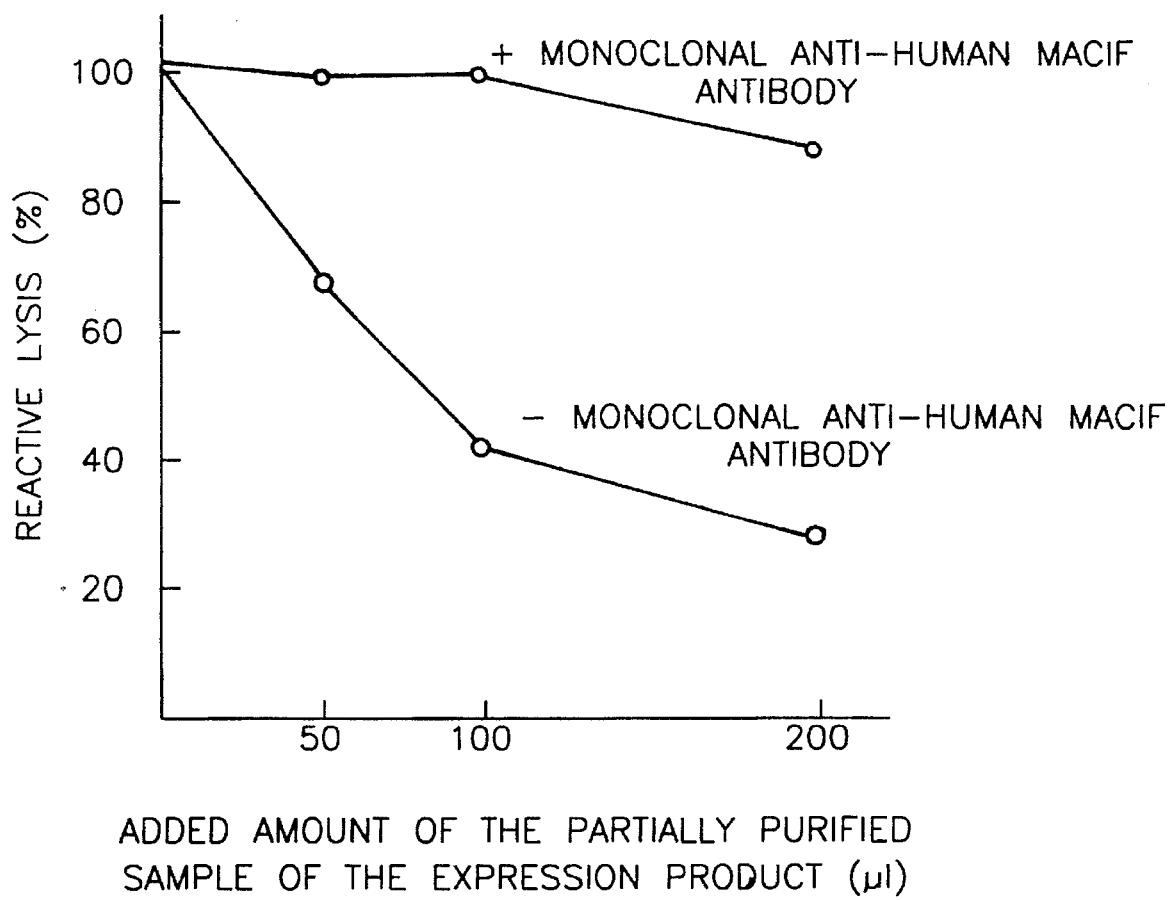
FIG. 13 illustrates the dose dependency of the inhibitory activity in hemolysis of guinea pig erythrocytes of the modified human MACIF protein E103 expressed in *Escherichia coli* and the result of neutralization thereof with an anti-human MACIF antibody.

As shown in FIG. 12, polyacrylamide gel electrophoresis performed in the presence of sodium dodecyl sulfate (SDS-PAGE) gave a main band in accord with the second activity peak. Therefore, these activity fractions were further purified on anti-human MACIF antibody column and reactive lysis inhibiting activity was measured in the same manner. As shown in FIG. 13, the purified expression product protein (E103) showed antihemolytic activity in a dose-dependent manner and the inhibitory activity was completely neutralized by the anti-human MACIF monoclonal antibody.

Figure 14:
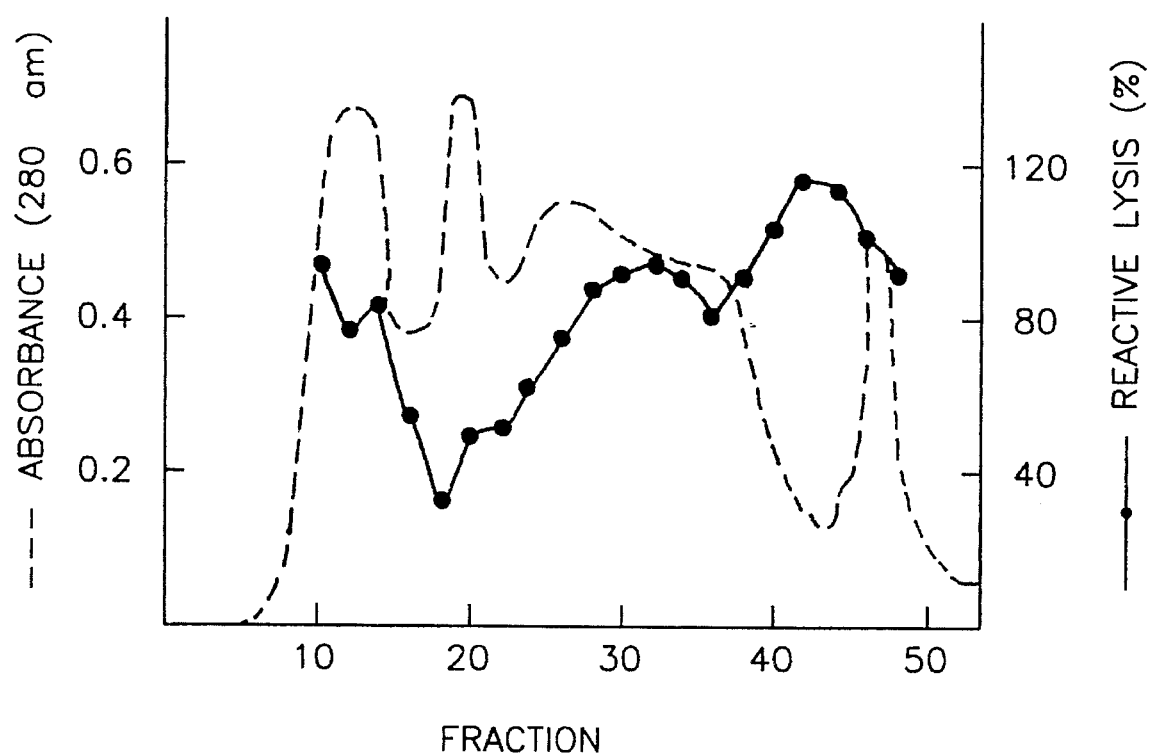
FIG. 14 illustrates the results of purification of a modified human MACIF protein (E86) expressed in *Escherichia coli* using Q-Sepharose.
Figure 15:
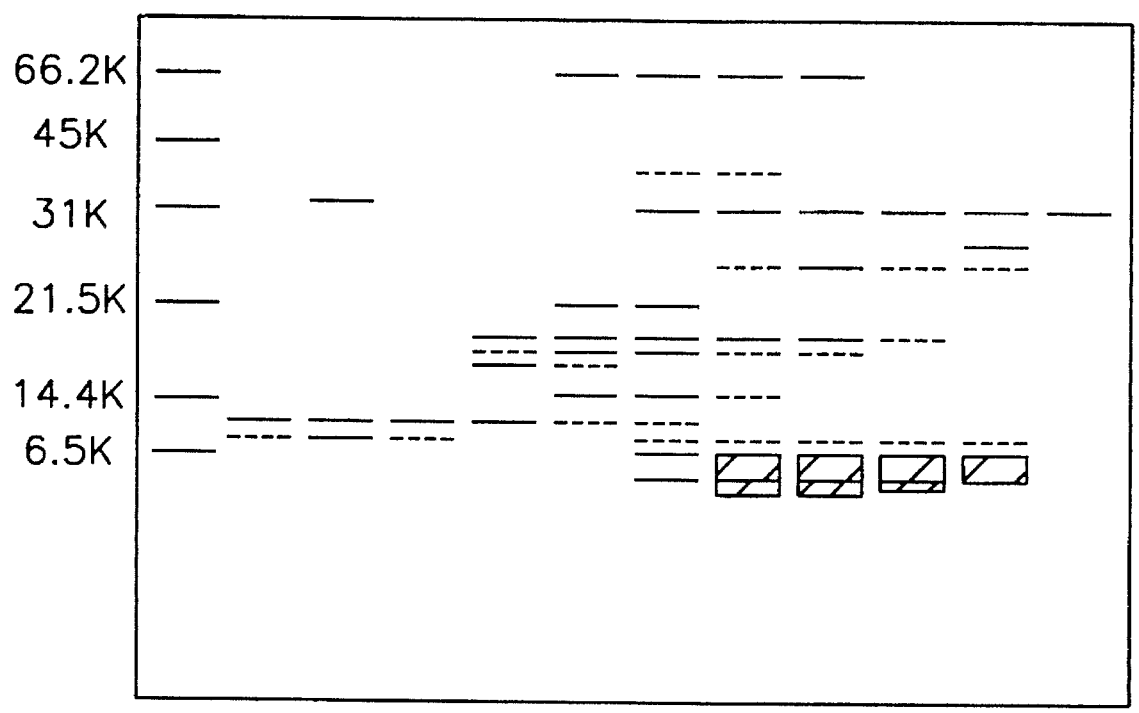
FIG. 15 illustrates the results of SDS-PAGE analysis of fractions obtained by purification of the modified human MACIF protein E86 expressed in *Escherichia coli* using Q-Sepharose.
Figure 16:
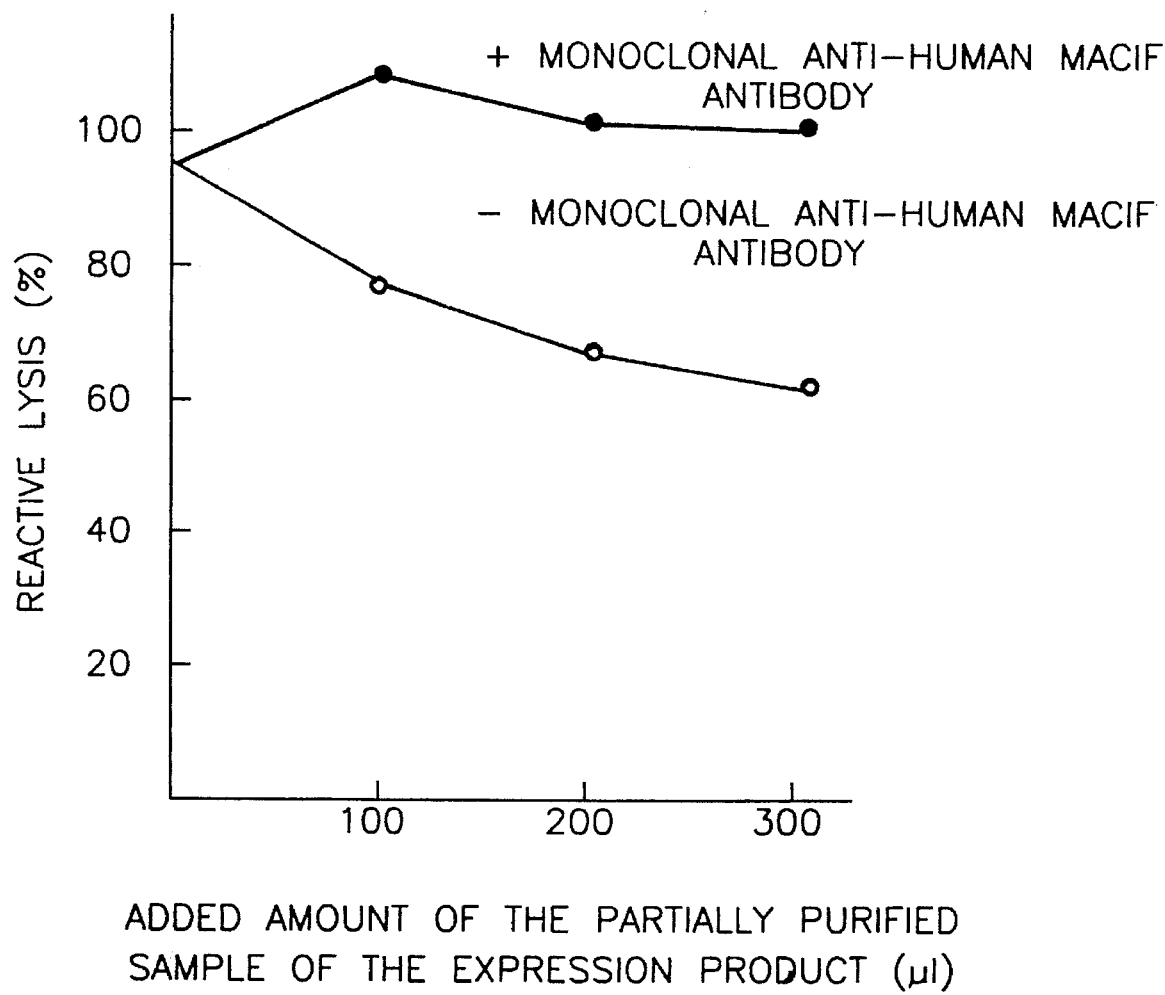
FIG. 16 illustrates the dose dependency of the inhibitory activity in hemolysis of guinea pig erythrocytes of the modified human MACIF protein E86 expressed in *Escherichia coli* and the result of neutralization thereof with an anti-human MACIF antibody.

2-3) Activity of the modified human MACIF protein (E86):

Unlike the case of E103, the activity data obtained failed to show a main peak of activity neutralizable by the antibody (FIG. 14). However, based on the results of SDS-PAGE analysis as shown in FIG. 15, the main band-containing fractions (Nos. 26–30) were purified on an anti-human MACIF antibody column, followed by reactive lysis inhibiting activity measurement. As shown in FIG. 16, the purified expression product protein (E86) showed antihemolytic activity in a dose-dependent manner. Furthermore, the inhibitory activity was completely neutralized by the antibody.

The above results indicate that the modified human MACIF protein expressed in *Escherichia coli* has the same activity as that of human erythrocyte-derived MACIF and that human MACIF can exhibit reactive lysis inhibiting activity even when it has no carbohydrate chain or no PI anchor.

(9) Expression of the gene coding for a modified human MACIF protein in CHO cells and confirmation of its biological activity:

1) Expression of a modified human MACIF protein (C86) in CHO cells:

1-1) Construction of a recombinant plasmid for expression in CHO cells:

The plasmid pVY1 obtained in section (6) was used as the vector for expression in CHO cells. Thus, pVY1 was cleaved with BglII and submitted to the following recombinant plasmid construction.

pGEM352-3 was cleaved with Ecg0109I and StyI and ligated with a synthetic DNA of the formula (VIII) phosphorylated at the StyI cleavage site and a synthetic DNA of the formula (IX) phosphorylated at the Eco0109I cleavage site, using T4 DNA ligase.

A DNA fragment of 341 base pairs was then isolated and purified by agarose gel electrophoresis. This DNA fragment was ligated with the BglII-cleaved pVY1 using T4 DNA ligase and the ligation mixture was used to transform *E. coli* HB101 to give tetracycline-resistant transformants. Plasmids were prepared therefrom by the alkaline bacteriolytic method and analyzed using restriction enzymes (PstI etc.) and a recombinant expression plasmid for the gene in question was selected out.

1-2) Confirmation of gene expression in CHO cells:

DHFR-deficient CHO cells (vide supra) were transfected with the expression plasmid constructed in the above manner by the calcium phosphate method. A transformant strain capable of growing in a selective medium [MEM alpha (−), Gibco] in the presence of methotrexate was obtained and used in the subsequent studies.

$10^8$ CHO cells transformed in the above manner were cultured and the culture supernatant was subjected to affinity chromatography using an anti-MACIF monoclonal antibody column and following the procedure described in section (5)-2-1). Fractions bound to this antibody column were eluted with 3M aqueous solution of sodium thiocyanate. Each eluate fraction was desalted on a PD-10 column (Pharmacia) and evaluated for the presence or absence of antigen by competitive ELISA using a rabbit anti-naturally occurring human MACIF antibody. As a result, it was confirmed that a human MACIF antigen was present in a "bound" fraction in the above affinity chromatography.

This result proves that a modified human MACIF protein comprising the peptide composed of the 1st to 86th amino acid residues had been successfully expressed in CHO cells in accordance with the invention.

2) Expression of a modified human MACIF protein (C82) in CHO cells:

2-1) Construction of a recombinant plasmid for expression in CHO cells:

The procedure of (9)-1-1) was repeated except that a DNA fragment of the formula (X) phosphorylated at the Eco0109I site was used in expression plasmid construction.

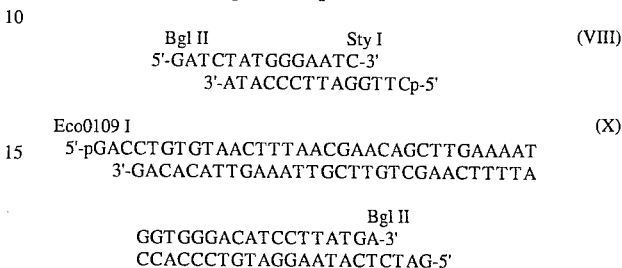

2-2) Confirmation of gene expression in CHO cells:

The procedure of (9)-1-2) was followed and a human MACIF antigen was detected in the culture supernatant obtained with CHO cells transformed with the above-mentioned recombinant vector. This result indicated that a modified human MACIF protein comprising the peptide composed of the 1st to 82nd amino acid residues had been successfully expressed in CHO cells in accordance with the present invention.

3) Expression of a modified human MACIF protein (C77) in CHO cells and confirmation of its biological activity:

3-1) Construction of a recombinant plasmid for gene expression in CHO cells:

The plasmid pVY1 obtained as described in the above (6) was used as the vector for gene expression in CHO cells. pVY1 was cleaved with BglII and submitted to the following recombinant plasmid construction.

pGEM352-3 was cleaved with Eco0109I and StyI and ligated with a synthetic DNA fragment of the formula (VIII) phosphorylated at the StyI cleavage site and a synthetic DNA fragment of the formula (XI) phosphorylated at the Eco0109I cleavage site, using T4 DNA ligase.

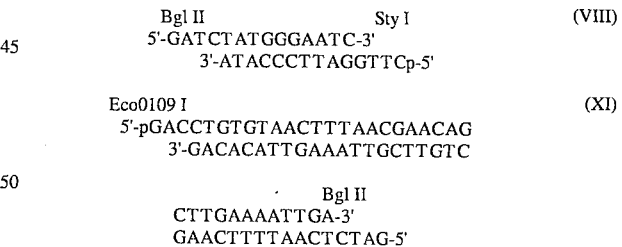

A DNA fragment of 314 base pairs was then isolated and purified by agarose gel electrophoresis. This DNA fragment was ligated with the BglII-cleaved pVY1 using T4 DNA ligase and the ligation mixture was used to transform *E. coli* HB101 to give tetracycline-resistant transformants. Plasmids were prepared from these by the alkaline bacteriolytic method and analyzed by using restriction enzymes (PstI etc.) and a recombinant plasmid capable of expression of the gene in question was selected out.

3-2) Confirmation of gene expression in CHO cells:

DHFR-deficient CHO cells (vide supra) were transfected with the expression plasmid constructed in the above manner by the calcium phosphate method and a transformant capable of growing in a selective medium [MEM alpha (−)

Gibco] in the presence of methotrexate was isolated and used for further studies.

$10^8$ CHO cells transformed by the above method were cultured and the culture supernatant was subjected to affinity chromatography using an anti-MACIF monoclonal antibody column and proceeding as described in (5)-2-1). Fractions bound to this antibody column were eluted with 3M aqueous solution of sodium thiocyanate and eluate fractions were desalted on a PD-10 column (Pharmacia) and assayed for the presence or absence of antigen by competitive ELISA using a rabbit anti-MACIF antibody. The presence of a MACIF antigen was confirmed in a "bound" fraction in the above affinity chromatography.

This result indicates that a modified human MACIF protein comprising the peptide composed of the 1st to 77th amino acid residues had been expressed successfully in CHO cells.

Figure 17:
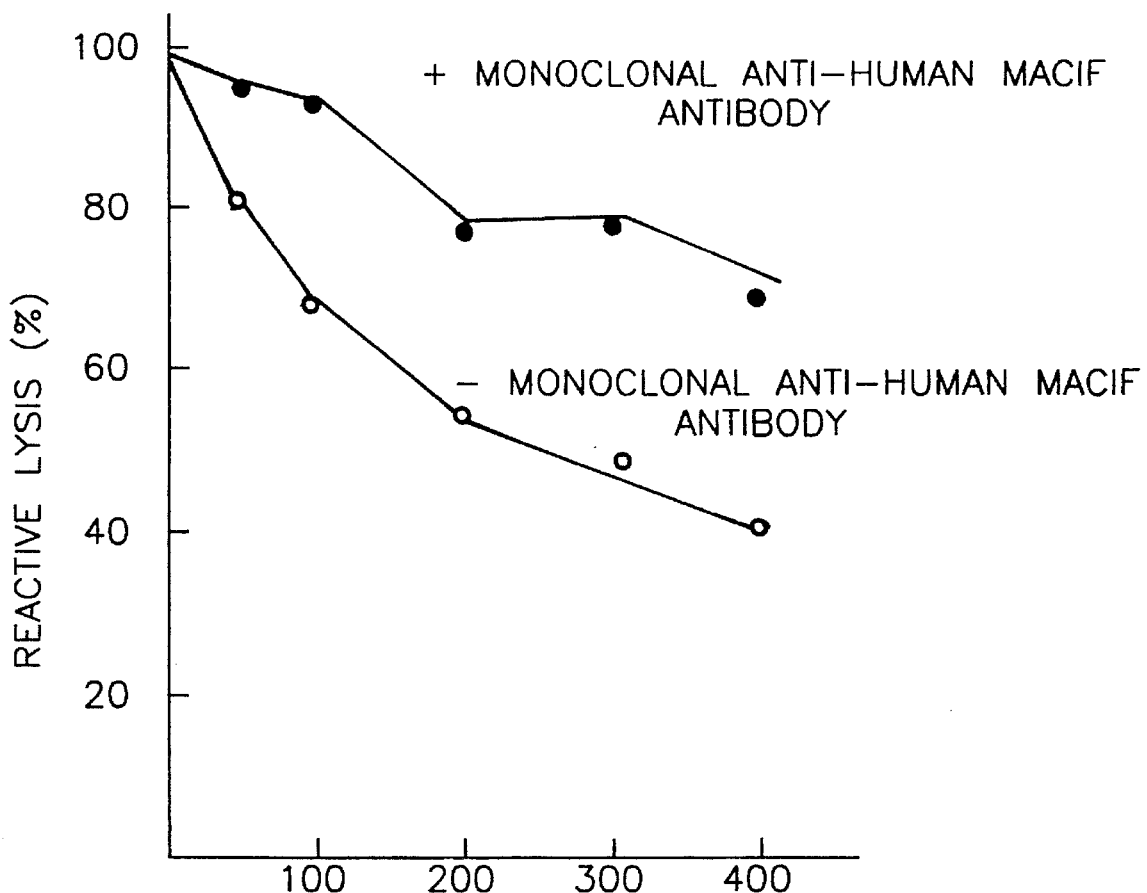
FIG. 17 illustrates the dose dependency of the inhibitory activity in hemolysis of guinea pig erythrocytes of the modified human MACIF protein (C77) expressed in transformant CHO cells and the results of a neutralization test thereof with an anti-human MACIF antibody.

3-3) Confirmation of biological activity:

A sample of the modified human MACIF protein C77 as partially purified from the culture supernatant resulting from mass culture of the transformed CHO cells by the purification procedure described in the above (9)-3-2) was subjected to buffer exchange for SGVB$^{2+}$, followed by MAC formation inhibiting activity assay, which was performed as described in (5)-2-2). As shown in FIG. 17, the modified human MACIF protein C77 expressed in CHO cells showed MAC formation inhibiting activity in a dose-dependent manner. The inhibitory activity was neutralized by a mouse monoclonal antibody to erythrocyte-derived, naturally occurring human MACIF.

From the above results, it is evident that the modified human MACIF protein C77 expressed in CHO cells and secreted into medium has the same activity as that of human erythrocyte-derived, naturally occurring MACIF.

4) Expression of a modified human MACIF protein (C76) in CHO cells and confirmation of its biological activity:

4-1) Construction of a recombinant plasmid for gene expression in CHO cells:

The procedure was the same as that described in (9)-1-1) except that a DNA fragment of the formula (XII) phosphorylated at the Eco0109I site was used in expression plasmid construction.

4-2) Confirmation of gene expression in CHO cells:

By following the procedure of (9)-1-2, a human MACIF antigen was detected in the culture supernatant resulting from cultivation of cells transformed with the above recombinant vector. This result indicates that a modified human MACIF protein comprising the peptide composed of the 1st to 76th amino acid residues had successfully been expressed in CHO cells.

Figure 18:
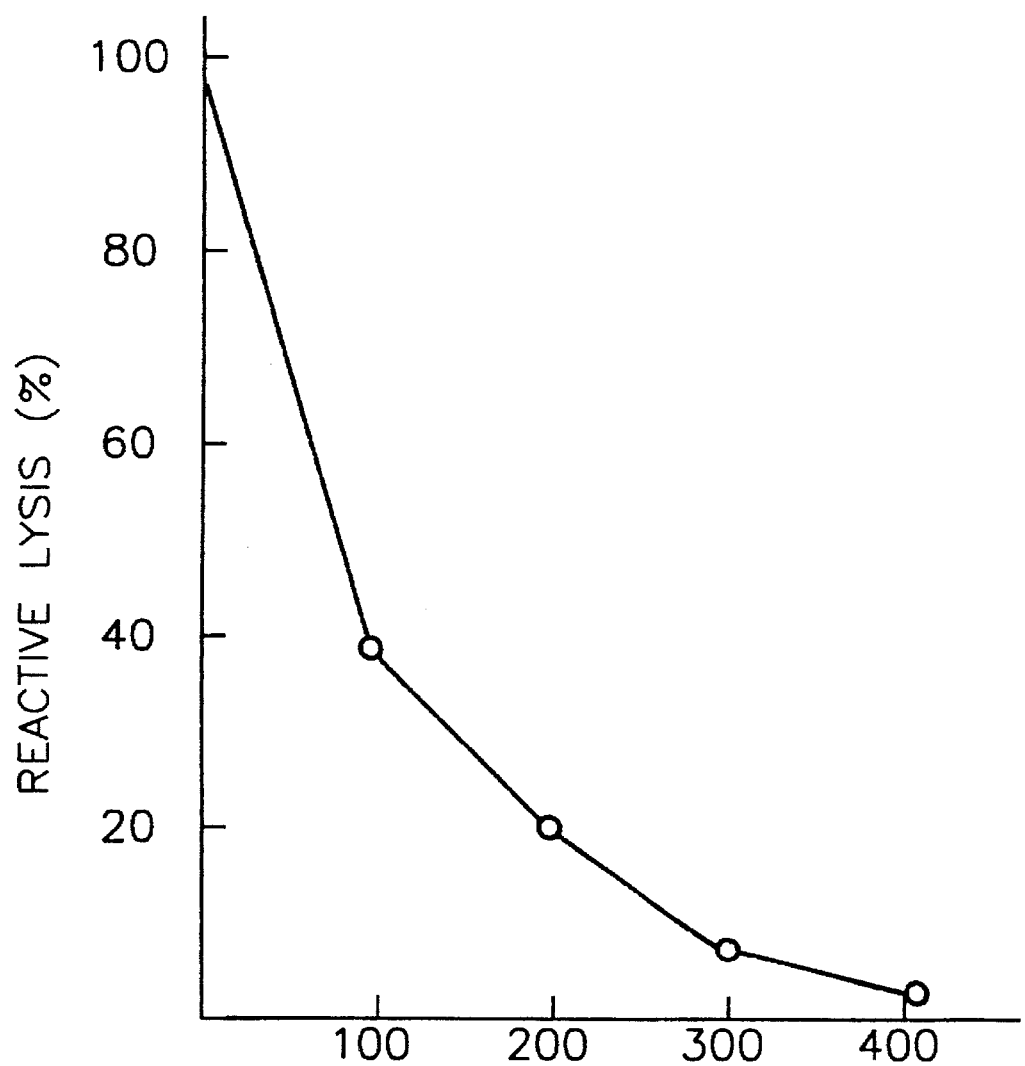
FIG. 18 illustrates the dose dependency of the inhibitory activity in hemolysis of guinea pig erythrocytes of the modified human MACIF protein (C76) expressed in transformant CHO cells.

4-3) Confirmation of biological activity:

The culture supernatant resulting from mass culture of the transformed CHO cells was used for evaluating the MAC formation inhibiting activity of the modified human MACIF protein (C76) expressed in CHO cells by following the procedure described in (9)-3-3). As shown in FIG. 18, C76 showed the activity in a dose-dependent manner.

From the results mentioned above, it is evident that the modified human MACIF protein (C76) expressed in CHO cells and secreted into medium has the same activity as that of human erythrocyte-derived, naturally occurring MACIF.

5) Expression of a modified human MACIF protein (C75) in CHO cells:

5-1) Construction of a recombinant plasmid for gene expression in CHO cells:

The procedure was the same as that described in (9)-1-1) except that a DNA fragment of the formula (XIII) phosphorylated at the Eco0109I site was used in expression plasmid construction.

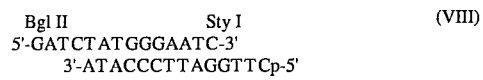

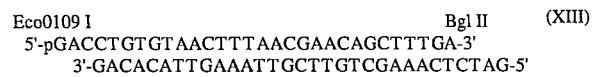

5-2) Confirmation of gene expression in CHO cells:

By following the procedure of (9)-1-2), a human MACIF antigen was detected in the culture supernatant obtained with cells transformed with the above-mentioned recombinant vector. This result indicates that a modified human MACIF protein comprising the peptide composed of the 1st to 75th amino acid residues had been successfully expressed in CHO cells.

6) Expression of a modified human MACIF protein (C70) in CHO cells and confirmation of its biological activity:

6-1) Construction of a recombinant plasmid for gene expression in CHO cells:

The procedure was the same as that described in (9)-1-1) except that a DNA fragment of the formula (XIV) phosphorylated at the Eco0109I site was used in expression plasmid construction.

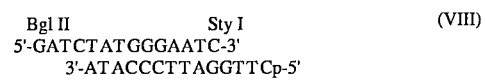

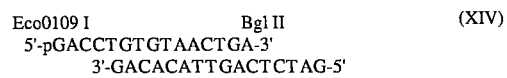

6-2) Confirmation of gene expression in CHO cells:

A human MACIF antigen was detected, by the procedure of (9)-1-2), in the culture supernatant obtained with cells transformed with the above recombinant vector. This result indicates that a modified human MACIF protein comprising the peptide composed of the 1st to 70th amino acid residues had been expressed successfully in CHO cells.

Figure 19:
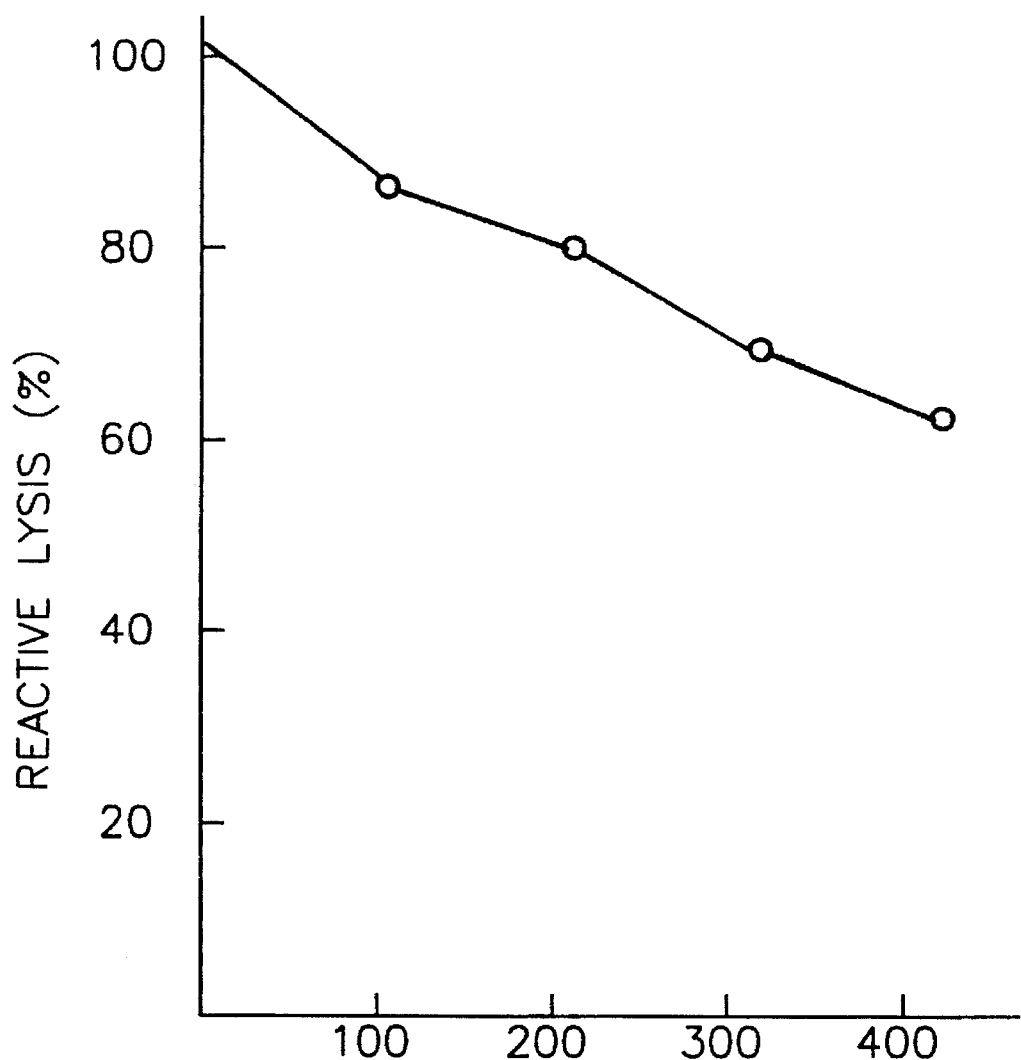
FIG. 19 illustrates the dose dependency of the inhibitory activity in hemolysis of guinea pig erythrocytes of the modified human MACIF protein (C70) expressed in transformant CHO cells.

6-3) Confirmation of biological activity:

The MAC formation inhibiting activity of the modified human MACIF protein (C70) expressed in CHO cells was measured using the culture supernatant obtained by mass culture of the transformed CHO cells and following the procedure of (9)-3-3). As shown in FIG. 19, C70 showed the activity in a dose-dependent manner.

From the results mentioned above, it is evident that the modified human MACIF protein (C70) expressed in CHO cells and secreted into medium has the same activity as that of human erythrocyte-derived, naturally occurring MACIF.

While the invention has been described in detail and with reference to specific embodiments thereof, it will be apparent to one skilled in the art that various changes and modifications can be made therein without departing from the spirit and scope thereof.

What is claimed is:

1. A fusion protein consisting of an N-terminal MACIF (Membrane Attack Complex Inhibition Factor) moiety having the following sequence:

```
  1    2    3    4    5    6    7    8    9   10
X-Leu  Gln  Cys  Tyr  Asn  Cys  Pro  Asn  Pro  Thr 11   12   13   14   15   16   17   18   19   20
Ala  Asp  Cys  Lys  Thr  Ala  Val  Asn  Cys  Ser 21   22   23   24   25   26   27   28   29   30
Ser  Asp  Phe  Asp  Ala  Cys  Leu  Ile  Thr  Lys 31   32   33   34   35   36   37   38   39   40
Ala  Gly  Leu  Gln  Val  Tyr  Asn  Lys  Cys  Trp 41   42   43   44   45   46   47   48   49   50
Lys  Phe  Glu  His  Cys  Asn  Phe  Asn  Asp  Val 51   52   53   54   55   56   57   58   59   60
Thr  Thr  Arg  Leu  Arg  Glu  Asn  Glu  Leu  Thr 61   62   63   64   65   66   67   68   69   70
Tyr  Tyr  Cys  Cys  Lys  Lys  Asp  Leu  Cys  Asn 71   72   73   74   75   76
Phe  Asn  Glu  Gln  Leu  Glu
``` wherein X is H or Met and a C-terminal moiety consisting of a heterologous phosphatidylinosirol (PI) anchor domain, wherein a PI membrane anchor is attached to said domain.

* * * * *